United States Patent
Zhang

(10) Patent No.: US 12,419,915 B2
(45) Date of Patent: Sep. 23, 2025

(54) MICROGLIAL PROGENITORS FOR REGENERATION OF FUNCTIONAL MICROGLIA IN THE CENTRAL NERVOUS SYSTEM AND THERAPEUTICS USES THEREOF

(71) Applicants: THE BROAD INSTITUTE, INC., Cambridge, MA (US); MASSACHUSETTS INSTITUTE OF TECHNOLOGY, Cambridge, MA (US)

(72) Inventor: Feng Zhang, Cambridge, MA (US)

(73) Assignees: THE BROAD INSTITUTE, INC., Cambridge, MA (US); MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 909 days.

(21) Appl. No.: 17/437,485

(22) PCT Filed: Mar. 13, 2020

(86) PCT No.: PCT/US2020/022805
§ 371 (c)(1),
(2) Date: Sep. 9, 2021

(87) PCT Pub. No.: WO2020/186237
PCT Pub. Date: Sep. 17, 2020

(65) Prior Publication Data
US 2022/0152115 A1 May 19, 2022

Related U.S. Application Data

(60) Provisional application No. 62/817,777, filed on Mar. 13, 2019.

(51) Int. Cl.
*A61K 35/28* (2015.01)
*C12N 5/0789* (2010.01)
*C12N 5/079* (2010.01)
*C12N 9/22* (2006.01)
*C12N 15/11* (2006.01)

(52) U.S. Cl.
CPC ............ *A61K 35/28* (2013.01); *C12N 5/0622* (2013.01); *C12N 5/0647* (2013.01); *C12N 9/22* (2013.01); *C12N 15/111* (2013.01); *C12N 2310/20* (2017.05); *C12N 2320/32* (2013.01); *C12N 2506/11* (2013.01); *C12N 2506/45* (2013.01); *C12N 2510/00* (2013.01)

(58) Field of Classification Search
CPC ...... C12N 5/0622; C12N 9/22; C12N 5/0647; C12N 15/111; C12N 2506/11; C12N 2506/45; C12N 2310/20; C12N 2510/00; C12N 2320/32; A61K 35/28
See application file for complete search history.

(56) References Cited

U.S. PATENT DOCUMENTS

| | | |
|---|---|---|
| 6,479,626 B1 | 11/2002 | Kim et al. |
| 6,534,261 B1 | 3/2003 | Cox et al. |
| 6,607,882 B1 | 8/2003 | Cox et al. |
| 6,746,838 B1 | 6/2004 | Choo et al. |
| 6,794,136 B1 | 9/2004 | Eisenberg et al. |
| 6,824,978 B1 | 11/2004 | Cox et al. |
| 6,866,997 B1 | 3/2005 | Choo et al. |
| 6,903,185 B2 | 6/2005 | Kim et al. |
| 6,933,113 B2 | 8/2005 | Case |
| 6,979,539 B2 | 12/2005 | Cox et al. |
| 7,013,219 B2 | 3/2006 | Case et al. |
| 7,030,215 B2 | 4/2006 | Liu et al. |
| 7,220,719 B2 | 5/2007 | Case et al. |
| 7,241,573 B2 | 7/2007 | Choo et al. |
| 7,241,574 B2 | 7/2007 | Choo et al. |
| 7,585,849 B2 | 9/2009 | Liu et al. |
| 7,595,376 B2 | 9/2009 | Kim et al. |
| 8,021,867 B2 | 9/2011 | Smith et al. |
| 8,119,361 B2 | 2/2012 | Smith et al. |
| 8,119,381 B2 | 2/2012 | Smith et al. |
| 8,124,369 B2 | 2/2012 | Smith et al. |
| 8,129,134 B2 | 3/2012 | Smith et al. |
| 8,133,697 B2 | 3/2012 | Smith et al. |
| 8,163,514 B2 | 4/2012 | Smith et al. |
| 8,372,951 B2 | 2/2013 | Chang et al. |
| 8,404,658 B2 | 3/2013 | Hajjar et al. |
| 8,440,431 B2 | 5/2013 | Voytas et al. |
| 8,440,432 B2 | 5/2013 | Voytas et al. |
| 8,450,471 B2 | 5/2013 | Voytas et al. |
| 8,454,972 B2 | 6/2013 | Nabel et al. |
| 9,956,247 B2* | 5/2018 | Rebar .................. A61P 3/00 |
| 2017/0253856 A1* | 9/2017 | Douvaras ............ A61P 25/00 |

FOREIGN PATENT DOCUMENTS

| | | |
|---|---|---|
| WO | 2014/093622 A2 | 6/2014 |
| WO | 2014/204725 A1 | 12/2014 |
| WO | 2016/094880 A1 | 6/2016 |
| WO | 2016/106236 A1 | 6/2016 |
| WO | 2016/161516 A1 | 10/2016 |
| WO | 2016/183841 A1 | 11/2016 |

(Continued)

OTHER PUBLICATIONS

Kiely et al. Early disease progression of Hurler syndrome. Oprhanet Journal of Rare Diseases (2017), 12:32. (Year: 2017).*

(Continued)

*Primary Examiner* — Sean C. Barron
(74) *Attorney, Agent, or Firm* — Johnson, Marcou, Isaacs & Nix, LLC; F. Brent Nix, Esq.

(57) ABSTRACT

Embodiments of the disclosure include compositions and methods for treating diseases (e.g., brain diseases) using genetic engineered cells. In some cases, the cells are engineered hematopoietic stem cells (HSCs), which are capable of engrafting to a central nervous system and differentiating to progeny cells (e.g., microglial cells).

20 Claims, No Drawings
Specification includes a Sequence Listing.

(56) References Cited

FOREIGN PATENT DOCUMENTS

| | | |
|---|---|---|
| WO | 2018/071898 A1 | 4/2018 |
| WO | 2018/187469 A1 | 10/2018 |
| WO | 2018/213708 A1 | 11/2018 |
| WO | 2018/213726 A1 | 11/2018 |
| WO | 2019/005884 A1 | 1/2019 |
| WO | 2019/005886 A1 | 1/2019 |
| WO | 2019/018423 A1 | 1/2019 |
| WO | 2019/060450 A1 | 3/2019 |
| WO | 2019/071048 A1 | 4/2019 |
| WO | 2019/126709 A1 | 6/2019 |
| WO | 2019/126716 A1 | 6/2019 |
| WO | 2019/126762 A2 | 6/2019 |
| WO | 2020/131862 A1 | 6/2020 |
| WO | 2020/186237 A1 | 9/2020 |

OTHER PUBLICATIONS

Lord et al. Autism Spectrum Disorder. The Lancet (2018), 392, 508-520. (Year: 2018).*

Eglitis et al. Hematopoietic cells differentiate into both microglia and macroglia in the brains of adult mice. PNAS (1997), 94, 4080-4085. (Year: 1997).*

Beutner et al. Generation of microglial cells from mouse embryonic stem cells. Nature Protocols (2010), 5(9), 1481-1494. (Year: 2010).*

Capotondo et al. Brain conditioning is instrumental for successful microglia reconstitution following hematopoietic stem cell transplantation. PNAS (2012), 109(37), 15018-15023. (Year: 2012).*

Hobbs et al. Reversal of Clinical Features of Hurler's Disease and Biochemical Improvement After Treatment By Bone-Marrow Transplantation. The Lancet (1981), 709-712. (Year: 1981).*

Pang et al. Human bone marrow hematopoietic stem cells are increased in frequency and myeloid-biased with age. PNAS (2011), 108(50), 20012-20017. (Year: 2011).*

NCBI gene entry to human CD28—Gene ID 940. Retrieved from https://web.archive.org/web/20161004005202/http://www.ncbi.nlm.nih.gov/gene/940 (Year: 2016).*

NCBI gene entry to human HLA-C—Gene ID 3107. Retrieved from https://web.archive.org/web/20150816003154/http://www.ncbi.nlm.nih.gov/gene/3107 (Year: 2015).*

Hirschi et al. Induced Pluripotent Stem Cells for Regenerative Medicine. Annu Rev Biomed Eng (2014), 16, 277-294. (Year: 2014).*

Aldenhoven et al. Quality of life of Hurler syndrome patients after successful hematopoietic stem cell transplantation. Blood Advances (2017), 1(24), 2236-2242. (Year: 2017).*

NCBI gene entry to mouse CD28—Gene ID 12487. Retrieved from https://web.archive.org/web/20150726033106/http://www.ncbi.nlm.nih.gov/gene/12487 (Year: 2015).*

NCBI gene entry to mouse PD-L1—Gene ID 60533. Retrieved fromhttps://web.archive.org/web/20140908153926/https://www.ncbi.nlm.nih.gov/gene/60533 (Year: 2014).*

El Yacoubi et al. Behavioral characterization of CD26 deficient mice in animal tests of anxiety and antidepressant-like activity. Behavioral Brain Research (2006), 171, 279-285. (Year: 2006).*

Tseng et al. Loss of Cxcl12/Sdf-1 in adult mice decreases the quiescent state of hematopoietic stem/progenitor cells and alters the pattern of hematopoietic regeneration after myelosuppression. Blood (2011), 117(2), 429-439. (Year: 2011).*

Ginhoux et al. Origin and differentiation of microglia. Frontiers in Cellular Neuroscience (2013), vol. 7, article 45. (Year: 2013).*

Nakazawa, "Microglia: a new target in the brain for depression, Alzheimer's, and more?" STAT Jan. 17, 2020, all enclosed pages cited.

"International Preliminary Report on Patentability issued in International Patent Application No. PCT/US2020/022805 filed Mar. 13, 2020", mailed Sep. 23, 2021, 11 pages.

"International Search Report and Written Opinion issued in International Patent Application No. PCT/US2020/022805 filed Mar. 13, 2020", mailed Jul. 2, 2020, 20 pages.

Akhavan, et al., "Car T Cells for Brain Tumors: Lessons Learned and Road Ahead", Immunological Reviews, vol. 290, 2019, 60-84.

Aleynik, et al., "Stem Cell Delivery of Therapies for Brain Disorders", Clinical and Translational Medicine, vol. 3, No. 24, 2014, 10 pages.

Anzalone, et al., "Search-and-replace Genome Editing Without Double-Strand Breaks or Donor DNA", Nature, vol. 576, No. 7785, Dec. 5, 2019, 149-157.

Atschul, et al., "Basic Local Alignment Search Tool", Journal of Molecular Biology, vol. 215, 1990, 403-410.

Basha, et al., "Influence of Cationic Lipid Composition on Gene Silencing Properties of Lipid Nanoparticle Formulations of siRNA in Antigen-Presenting Cells", Molecular Therapy, vol. 19, No. 12, Dec. 2011, 2186-2200.

Bates, et al., "Carbon Nanotubes as Vectors for Gene Therapy: Past Achievements, Present Challenges and Future Goals", Advanced Drug Delivery Reviews, vol. 65, 2013, 2023-2033.

Bennett, et al., "New Tools for Studying Microglia in the Mouse and Human CNS", Proceedings of the National Academy of Sciences of the United States of America, vol. 113, No. 12, Mar. 22, 2016, E1738-E1746.

Bhujbal, et al., "Drug and Cell Encapsulation: Alternative Delivery Options for the Treatment of Malignant Brain Tumors", Advanced Drug Delivery Reviews, vol. 67-68, Apr. 2014, 142-153.

Biffi, et al., "Correction of Established Neurologic Disease and Evidences of In Vivo Cross Correction in the Mouse Model of Metachromatic Leukodystrophy", Molecular Therapy, vol. 13, Suppl 1, 891, May, 1118-1129.

Biswass, et al., "CRISPRTarget: Bioinformatic Prediction and Analysis of crRNA Targets", RNA Biology, vol. 10, No. 5, May 2013, 817-827.

Capotondo, et al., "Intracerebroventricular Delivery of Hematopoietic Progenitors Results in Rapid and Robust Engraftment of Microglia-Like Cells", Science Advances, vol. 3, No. 12, Dec. 2017, 12 pages.

Carr, et al., "Genome Engineering", Nature Biotechnology, vol. 27, No. 12, Dec. 9, 2009, 1151-1162.

Cartier, et al., "Hematopoietic Stem Cell Gene Therapy with a Lentiviral Vector in X-Linked Adrenoleukodystrophy", Science, vol. 326, Nov. 6, 2009, 818-823.

Cermak, et al., "Efficient Design and Assembly of Custom TALEN and Other TAL Effector-Based Constructs for DNA Targeting", Nucleic Acids Research, vol. 39, No. 12, e82, Jul. 2011, 11 pages.

Choi, et al., "Targeted Genomic Rearrangements Using CRISPR/Cas Technology", Nature Communications. Vol. 5. No. 3728, 2014, 9 pages.

Cox, et al., "RNA Editing with CRISPR-Cas13", Science, vol. 358, No. 6366, Nov. 24, 2017, 1019-1027.

D'astolfo, et al., "Efficient Intracellular Delivery of Native Proteins", Cell, vol. 161, 2015, 674-690.

Derecki, et al., "Wild-Type Microglia Arrest Pathology in a Mouse Model of Rett Syndrome", Nature, vol. 484, No. 7392, Mar. 18, 2012, 15 pages.

Digiusto, et al., "RNA-Based Gene Therapy for HIV with Lentiviral Vector-Modified CD34(+) Cells in Patients Undergoing Transplantation for AIDSrelated Lymphoma", Science Translational Medicine, vol. 2, Issue 36, Jun. 16, 2010, 8 pages.

Doench, et al., "Rational Design of Highly Active SgRNAs for CRISPR-Cas9-Mediated Gene Inactivation", Nature Biotechnology, vol. 32, No. 12, Dec. 2014, 17 pages.

Dong, Xiaowei, "Current Strategies for Brain Drug Delivery", Theranostics, vol. 8, Issue 6, Feb. 2018, 1481-1493.

Douvaras, et al., "Directed Differentiation of Human Pluripotent Stem Cells to Microglia", Stem Cell Reports, vol. 8, Jun. 6, 2017, 1516-1524.

Doyon, et al., "Enhancing Zinc-Finger-Nuclease Activity With Improved Obligate Heterodimeric Architectures", Nature Methods, vol. 8, No. 1, Jan. 2011, 74-79.

Du, et al., "Label-Free Dendrimer-like Silica Nanohybrids for Traceable and Controlled Gene Delivery", Biomaterials, vol. 35, Issue 21, Jul. 2014, 5580-5590.

Eglitis, et al., "Hematopoietic Cells Differentiate into Both Microglia and Macroglia in the Brains of Adult Mice", Proceedings of the National Academy of Sciences, vol. 94, Apr. 1997, 4080-4085.

(56) References Cited

OTHER PUBLICATIONS

Esvelt, et al., "Orthogonal Cas9 Proteins for RNA-Guided Gene Regulation and Editing", Nature Methods, vol. 10, No. 11, Nov. 2013, 19 pages.
Gao, et al., "Engineered Cpf1 Enzymes with Altered PAM Specificities", BioRxiv, Dec. 4, 2016, 17 pages.
Gaudelli, et al., "Programmable Base Editing of A•T to G•C in Genomic DNA Without DNA Cleavage", Nature, vol. 551, No. 7681, Nov. 23, 2017, 464-471.
Gleditzsch, et al., "PAM Identification by CRISPR-Cas Effector Complexes: Diversified Mechanisms and Structures", RNA Biology, vol. 16. No. 4, 2019, 504-517.
Gray, et al., "Viral Vectors and Delivery Strategies for CNS Gene Therapy", Therapeutic Delivery, vol. 1, Issue No. 4, Oct. 2010, 517-534.
Grimm, et al., "In Vitro and In Vivo Gene Therapy Vector Evolution via Multispecies Interbreeding and Retargeting of Adeno-Associated Viruses", Journal of Virology, vol. 82, No. 12, Jun. 2008, 5887-5911.
Grissa, et al., "CRISPRFinder: A Web Tool to Identify Clustered Regularly Interspaced Short Palindromic Repeats", Nucleic Acids Research, vol. 35, Jul. 1, 2007, W52-W57.
Gruber, et al., "The Vienna RNA Websuite", Nucleic Acids Research, vol. 36, Apr. 19, 2008, W70-W74.
Jiang, et al., "RNA-Guided Editing of Bacterial Genomes Using CRISPR-Cas Systems", Nature Biotechnology, vol. 31, No. 3, Mar. 2013, 233-239.
Kim, et al., "Chimeric Restriction Endonuclease", Proceedings of the National Academy of Sciences, vol. 91, No. 3, 1994, 883-887.
Kim, et al., "Hybrid Restriction Enzymes: Zinc Finger Fusions to Fok I Cleavage Domain", Proceedings of the National Academy of Sciences, vol. 93 No. 3, Feb. 1996, 1156-1160.
Kleinstiver, et al., "Engineered Crispr-Cas9 Nucleases with Altered Pam Specificities", Nature, vol. 523, No. 7561, Jul. 23, 2015, 481-485.
Klompe, et al., "Transposon-encoded CRISPR-Cas Systems Direct RNA-guided DNA Integration", Nature, vol. 571, Jul. 11, 2019, 219-225.
Kogure, et al., "Development of a Non-Viral Multifunctional Envelope-Type Nano Device by a Novel Lipid Film Hydration Method", Journal of Controlled Release, vol. 98, Issue 2, Aug. 2004, 317-323.
Komor, et al., "Programmable Editing of a Target Base in Genomic DNA without Double-Stranded DNA Cleavage", Nature, vol. 533, No. 7603, May 19, 2016, 420-424.
Koonin, et al., "Origins and Evolution of CRISPR-Cas Systems", Philosophical Transactions of the Royal Society of London, vol. 374, No. 1772, May 13, 2019, 16 pages.
Korzhevskii, et al., "Brain Microglia and Microglial Markers", Neuroscience and Behavioral Physiology, vol. 46, No. 3, Mar. 2016, 284-290.
Lee, et al., "Improved Ex Vivo Expansion of Adult Hematopoietic Stem Cells by Overcoming CUL4-Mediated Degradation of HOXB4", Blood, vol. 121, No. 20, May 16, 2013, 4082-4089.
Lee, et al., "Nanoparticle Delivery of Cas9 Ribonucleoprotein and Donor DNA in Vivo Induces Homology-Directed DNA Repair", Nature Biomedical Engineering, vol. 1, 2017, 889-901.
Leenay, et al., "Identifying and Visualizing Functional PAN Diversity across Crispr-Cas Systems", Molecular Cell, vol. 62, No. 1, Apr. 7, 2016, 137-147.
Levy, et al., "Cytosine and Adenine Base Editing of the Brain, Liver, Retina, Heart and Skeletal Muscle of Mice via Adeno-Associated Viruses", Nature Biomedical Engineering, vol. 4, 2020, 97-110.
Li, et al., "Base Editing With a Cpf1-cytidine Deaminase Fusion", Nature Biotechnology, vol. 36, Apr. 2018, 324-327.
Lino, et al., "Delivering Crispr: A Review of the Challenges and Approaches", Drug Delivery, vol. 25, No. 1, Nov. 2018, 1234-1257.
Liu, et al., "Engineering Cell Signaling Using Tunable CRISPR-Cpf1-based Transcription Factors", Nature Communications, vol. 8, No. 2095, Dec. 13, 2017, 8 pages.
Luo, et al., "Enhancement of Transfection by Physical Concentration of DNA at the Cell Surface", Nature Biotechnology, vol. 18, 2000, 893-895.
Luo, et al., "Multifunctional Enveloped Mesoporous Silica Nanoparticles for Subcellular Co-Delivery of Drug and Therapeutic Peptide", Scientific Reports, vol. 4, Article No. 6064, Aug. 14, 2014, 10 pages.
Makarova, et al., "Classification and Nomenclature of CRISPR-Cas Systems: Where from Here?", The CRISPR Journal, vol. 1, No. 5, 2018, 325-336.
Makarova, et al., "Evolutionary Classification of CRISPR-Cas Systems: A Burst of Class 2 and Derived Variants", Nature Reviews Microbiology, vol. 18, Feb. 2020, 67-83.
Marraffini, et al., "Self Vs. Non-Self Discrimination During CRISPR RNA-Directed Immunity", Nature, vol. 463, No. 7280, Jan. 28, 2010, 568-571.
Miura, et al., "Monitoring Early Differentiation Events in Human Embryonic Stem Cells by Massively Parallel Signature Sequencing and Expressed Sequence Tag Scan", Stem Cells and Developmentvol. 13, No. 6, 2004, 694-715.
Mojica, et al., "Short Motif Sequences Determine the Targets of the Prokaryotic CRISPR Defence System", Microbiology, vol. 155, 2009, 733-740.
Moscou, et al., "A Simple Cipher Governs DNA Recognition by TAL Effectors", Science, vol. 326, Issue 5959, Dec. 11, 2009, 1501 page.
Mout, et al., "Direct Cytosolic Delivery of CRISPR/Cas9-Ribonucleoprotein for Efficient Gene Editing", ACS Nano, vol. 11, No. 3, Mar. 28, 2017, 2452-2458.
Nakagawa, et al., "Generation of Induced Pluripotent Stem Cells Without Myc from Mouse and Human Fibroblasts", Nature Biotechnology, vol. 26, No. 1, Jan. 2008, 101-106.
Nakamura, et al., "A Multifunctional Envelope-type Nanodevice for Use in Nanomedicine: Concept and Applications", Accounts of Chemical Research, vol. 45, No. 7, 2012, 1113-1121.
Neal et al., "An Update on Intracerebral Stem Cell Grafts", Expert Review of Neurotherapeutics, vol. 18, Issue 7, 2018, 557-572.
Nishida, et al., "Targeted Nucleotide Editing Using Hybrid Prokaryotic and Vertebrate Adaptive Immune Systems", Science, vol. 353, Issue. 6305, Sep. 16, 2016, 35 pages.
Nishimasu, et al., "Crystal Structure of Cas9 in Complex with Guide RNA and Target DNA", Cell, vol. 156, Feb. 27, 2014, 935-949.
Okita, et al., "Generation of Germline-Competent Induced Pluripotent Stem Cells", Nature, vol. 448, No. 7151, 2007, 313-317.
Pandya, et al., "Differentiation of Human and Murine Induced Pluripotent Stem Cells to Microglia-like Cells", Nature Neurocience, vol. 20, No. 5, May 2017, 28 pages.
Patel, et al., "Getting into the Brain: Approaches to Enhance Brain Drug Delivery", CNS Drugs, vol. 23, No. 1, 2009, 35-58.
Pattanayak, et al., "High-Throughput Profiling of Off-Target DNA Cleavage Reveals RNA-Programmed Cas9 Nuclease Specificity", Nature Biotechnology, vol. 31, No. 9, Sep. 2013, 839-843.
Peters, et al., "Recruitment of CRISPR-Cas Systems by Tn7-Like Transposons", Proceedings of the National Academy of Sciences, vol. 114, No. 35, 2017, E7358-E7366.
Pocock, et al., "Modelling Microglial Function with Induced Pluripotent Stem Cells: An Update", Nature Reviews Neuroscience, vol. 19, 2018, 445-452.
Qui, et al., "Mutation Detection Using Surveyor Nuclease", Biotechniques, vol. 36, No. 4, 2004, 702-707.
Ran, et al., "Double Nicking by RNA-Guided CRISPR Cas9 for Enhanced Genome Editing Specificity", Cell, vol. 154, No. 6, Sep. 12, 2013, 1380-1389.
Rees, et al., "Base Editing: Precision Chemistry on The Genome and Transcriptome of Living Cells", Nature Reviews Genetics, vol. 19, No. 12, Dec. 2018, 770-788.
Shmakov, et al., "Discovery and Functional Characterization of Diverse Class 2 CRISPR-Cas Systems", Molecular Cell, vol. 60, No. 3, Nov. 5, 2015, 385-397.
Sierig, et al., "Cytotoxic Effects of Streptolysin O and Streptolysin S Enhance the Virulence of Poorly Encapsulated Group a Streptococci", Infection and Immunity, vol. 71, No. 1, Jan. 2003, 446-455.

(56) References Cited

OTHER PUBLICATIONS

Strecker, et al., "RNA-Guided DNA Insertion with CRiSPR-Associated Transposes", Science, 10/1126/science.aax9181, 2019, 12 pages.

Sun, et al., "Cocoon-like Self-Degradable Dna Nanoclew for Anticancer Drug Delivery", Journal of the American Chemical Society, vol. 136, No. 42, Oct. 13, 2014, 14722-14725.

Sun, et al., "Self-Assembled Dna Nanoclews for the Efficient Delivery of Crispr-cas9 for Genome Editing", Angewandte Chemie International Edition, vol. 54, Issue 41, Oct. 5, 2015, 12029-12033.

Suzuki, et al., "In Vivo Genome Editing Via CRISPR/Cas9 Mediated Homology-Independent Targeted Integration", Nature, vol. 540, Dec. 2016, 144-149.

Takahashi, et al., "Induction of Pluripotent Stem Cells from Adult Human Fibroblasts by Defined Factors", Cell, vol. 131, Issue 5, Nov. 30, 2007, 861-872.

Takahashi, et al., "Induction of Pluripotent Stem Cells from Mouse Embryonic and Adult Fibroblast Cultures by Defined Factors", Cell, vol. 126, Issue 4, Aug. 25, 2006, 663-676.

Teng, et al., "Labeling Proteins Inside Living Cells Using External Fluorophores for Fluorescence Microscopy", Elife 6:e25460, 2016, 13 pages.

Vitry, et al., "Primordial Hematopoietic Stem Cells Generate Microglia But Not Myelin-Forming Cells in a Neural Environment", The Journal of Neuroscience, vol. 23, No. 33, Nov. 19, 2003, 10724-10731.

Walev, et al., "Delivery of Proteins into Living Cells by Reversible Membrane Permeabilization with Streptolysin-O", PNAS, vol. 98, No. 6, Mar. 13, 2001, 3185-3190.

Wang, et al., "RNA-Guided Endonuclease Provides a Therapeutic Strategy to Cure Latent Herpesviridae Infection", PNAS, vol. 111, No. 36, Sep. 9, 2014, 13157-13162.

Wu, et al., "Correction of a Genetic Disease by CRISPR-Cas9-Mediated Gene Editing in Mouse Spermatogonial Stem Cells", Cell Research, vol. 25, 2015, 67-79.

Yasunaga, et al., "Induction and Monitoring of Definitive and Visceral Endoderm Differentiation of Mouse ES Cells", Nature Biotechnology, vol. 23, No. 12, 2005, 1542-1550.

Ye, et al., "Seamless Modification of Wild-Type Induced Pluripotent Stem Cells to the Natural CCR5Δ32 Mutation Confers Resistance to HIV Infection", PNAS, vol. 111, No. 26, Jul. 1, 2014, 9591-9596.

Yu, et al., "Induced Pluripotent Stem Cell Lines Derived From Human Somatic Cells", Science, vol. 318, No. 5858, Dec. 2007, 1917-1920.

Zetche, et al., "A Split Cas9 Architecture for Inducible Genome Editing and Transcription Modulation", Nature Biotechnology, vol. 33, No. 2, Feb. 2015, 139-142.

Zetsche, et al., "Cpf1 is a Single RNA-Guided Endonuclease of a Class 2 CRISPR-Cas System", Cell, vol. 163, No. 3, Oct. 22, 2015, 759-771.

Zhang, et al., "Efficient Construction of Sequence-Specific TAL Effectors for Modulating Mammalian Transcription", Nature Biotechnology, vol. 29, No. 2, Feb. 2011, 149-153.

Zheng, et al., "Differentiation of Glial Cells From hiPSCs: Potential Applications in Neurological Diseases and Cell Replacement Therapy", Frontiers in Cellular Neuroscience, vol. 12, Article 239, Aug. 2018, 21 pages.

Zuckermann, et al., "Somatic CRISPR/Cas9-Mediated Tumour Suppressor Disruption Enables Versatile Brain Tumour Modelling", Nature Communications, vol. 6, No. 7391, Jun. 11, 2015,.

Zuker, et al., "Optimal Computer Folding of Large RNA Sequences Using Thermodynamics and Auxiliary Information", Nucleic Acids Research, vol. 9, No. 1, 1981, 133-148.

USPTO Subject Matter Eligibility Examination Guidance, Nature-Based Products Example 5, pp. 27-28.

* cited by examiner

SEQUENCE LISTING

<160> NUMBER OF SEQ ID NOS: 17

<210> SEQ ID NO 1
<211> LENGTH: 7
<212> TYPE: PRT
<213> ORGANISM: Simian virus 40

<400> SEQUENCE: 1

Pro Lys Lys Lys Arg Lys Val
1               5

<210> SEQ ID NO 2
<211> LENGTH: 16
<212> TYPE: PRT
<213> ORGANISM: Artificial Sequence
<220> FEATURE:
<223> OTHER INFORMATION: Synthetic

<400> SEQUENCE: 2

Lys Arg Pro Ala Ala Thr Lys Lys Ala Gly Gln Ala Lys Lys Lys Lys
1               5                   10                  15

<210> SEQ ID NO 3
<211> LENGTH: 9
<212> TYPE: PRT
<213> ORGANISM: Homo sapiens

<400> SEQUENCE: 3

Pro Ala Ala Lys Arg Val Lys Leu Asp
1               5

<210> SEQ ID NO 4
<211> LENGTH: 11
<212> TYPE: PRT
<213> ORGANISM: Homo sapiens

<400> SEQUENCE: 4

Arg Gln Arg Arg Asn Glu Leu Lys Arg Ser Pro
1               5                   10

<210> SEQ ID NO 5
<211> LENGTH: 38
<212> TYPE: PRT
<213> ORGANISM: Homo sapiens

<400> SEQUENCE: 5

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
            20                  25                  30

Arg Asn Gln Gly Gly Tyr
        35

<210> SEQ ID NO 6
<211> LENGTH: 42
<212> TYPE: PRT
<213> ORGANISM: Homo sapiens

<400> SEQUENCE: 6

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

```
Asp Glu Gln Ile Leu Lys Arg Arg Asn Val
            35                  40
```

```
<210> SEQ ID NO 7
<211> LENGTH: 8
<212> TYPE: PRT
<213> ORGANISM: Homo sapiens

<400> SEQUENCE: 7

Val Ser Arg Lys Arg Pro Arg Pro
1               5
```

```
<210> SEQ ID NO 8
<211> LENGTH: 8
<212> TYPE: PRT
<213> ORGANISM: Homo sapiens

<400> SEQUENCE: 8

Pro Pro Lys Lys Ala Arg Glu Asp
1               5
```

```
<210> SEQ ID NO 9
<211> LENGTH: 8
<212> TYPE: PRT
<213> ORGANISM: Homo sapiens

<400> SEQUENCE: 9

Pro Gln Pro Lys Lys Lys Pro Leu
1               5
```

```
<210> SEQ ID NO 10
<211> LENGTH: 12
<212> TYPE: PRT
<213> ORGANISM: Mus sp.

<400> SEQUENCE: 10

Ser Ala Leu Ile Lys Lys Lys Lys Met Ala Pro
1               5                   10
```

```
<210> SEQ ID NO 11
<211> LENGTH: 5
<212> TYPE: PRT
<213> ORGANISM: Influenza virus

<400> SEQUENCE: 11

Asp Arg Leu Arg Arg
1               5
```

```
<210> SEQ ID NO 12
<211> LENGTH: 7
<212> TYPE: PRT
<213> ORGANISM: Influenza virus

<400> SEQUENCE: 12

Pro Lys Gln Lys Lys Arg Lys
1               5
```

```
<210> SEQ ID NO 13
<211> LENGTH: 10
<212> TYPE: PRT
<213> ORGANISM: Hepatitis delta virus

<400> SEQUENCE: 13

Arg Lys Leu Lys Lys Lys Ile Lys Lys Leu
1               5                   10
```

```
<210> SEQ ID NO 14
<211> LENGTH: 10
<212> TYPE: PRT
<213> ORGANISM: Mus sp.

<400> SEQUENCE: 14

Arg Glu Lys Lys Lys Phe Leu Lys Arg Arg
1               5                   10

<210> SEQ ID NO 15
<211> LENGTH: 20
<212> TYPE: PRT
<213> ORGANISM: Homo sapiens

<400> SEQUENCE: 15

Lys Arg Lys Gly Asp Glu Val Asp Gly Val Asp Glu Val Ala Lys Lys
1               5                   10                  15

Lys Ser Lys Lys
            20

<210> SEQ ID NO 16
<211> LENGTH: 17
<212> TYPE: PRT
<213> ORGANISM: Homo sapiens

<400> SEQUENCE: 16

Arg Lys Cys Leu Gln Ala Gly Met Asn Leu Glu Ala Arg Lys Thr Lys
1               5                   10                  15

Lys

<210> SEQ ID NO 17
<211> LENGTH: 10
<212> TYPE: PRT
<213> ORGANISM: Simian virus 40

<400> SEQUENCE: 17

Pro Lys Lys Lys Arg Lys Val Glu Ala Ser
1               5                   10
```

MICROGLIAL PROGENITORS FOR REGENERATION OF FUNCTIONAL MICROGLIA IN THE CENTRAL NERVOUS SYSTEM AND THERAPEUTICS USES THEREOF

CROSS-REFERENCE TO RELATED APPLICATIONS

This application is a U.S. national stage entry of International Application Number PCT/US2020/022805 filed Mar. 13, 2020, which claims the benefit of U.S. Provisional Application No. 62/817,777, filed Mar. 13, 2019. The entire contents of the above-identified applications are hereby fully incorporated herein by reference.

STATEMENT REGARDING FEDERALLY SPONSORED RESEARCH

This invention was made with government support under Grant Nos. HL141201 and MH110049 awarded by the National Institutes of Health. The government has certain rights in the invention.

REFERENCE TO AN ELECTRONIC SEQUENCE LISTING

The contents of the electronic sequence listing ("BROD-2565US_ST25.txt"; Size is 3,771 bytes and it was created on Jul. 8, 2025) is herein incorporated by reference in its entirety.

TECHNICAL FIELD

The subject matter disclosed herein is generally directed to treating diseases (e.g., brain disease) using engineered cells.

BACKGROUND

A number of brain disorders may be caused by microglial dysfunction, including Schizophrenia, Alzheimer's Disease, some forms of Autism Spectrum Disorder (e.g., Rett Syndrome), and lysosomal storage diseases (e.g. Hurler's syndrome). Adult hematopoietic stem cells (HSCs) can give rise to new microglial cells in the brain. Although most microglial cells in the brain are regenerated from resident microglial progenitor cells, it is observed in mouse that some adult myeloid can engraft in the adult brain as microglial cells. This phenomenon opens the opportunity to engraft wild-type or healthy microglia in the brain to treat diseases that are resulting from dysfunctional microglial cells. However, the use of HSCs to regenerate microglial cells faces challenges such as low efficiency of engraftment and donor cells shortage. New approaches are needed to overcome these challenges.

SUMMARY

In general, the present disclosure provides methods and compositions for treating diseases in the central nervous system (CNS). In one aspect, the present disclosure includes a composition comprising an engineered cell designed to infiltrate or engraft in the CNS of a subject and differentiate into a microglial cell that treats and/or ameliorates a disease or disorder of the CNS in the subject.

In some embodiments, the engineered cell comprises a hematopoietic stem cell (HSC). In some embodiments, the engineered cell is capable of engrafting in the brain or spinal cord. In some embodiments, the engineered cell is designed to treat or ameliorate a lysosomal storage disease. In some embodiments, the engineered cell is engineered to produce a protein suitable for enzyme replacement therapy. In some embodiments, the lysosomal storage disease is Hurler's syndrome.

In some embodiments, the engineered cell is designed to treat or ameliorate schizophrenia. In some embodiments, the engineered cell is designed to treat or ameliorate an autism spectrum disorder. In some embodiments, the autism spectrum disorder is Rett Syndrome. In some embodiments, the engineered cell is designed to treat Alzheimer's disease. In some embodiments, the engineered cell is from or derived from the subject. In some embodiments, the engineered cell is from or derived from a donor subject of the same species as the subject.

In some embodiments, the engineered cell is from or derived from a donor subject of a different species as the subject. In some embodiments, one or more immunogenic genes in the engineered cell is deleted. In some embodiments, one or more of immunogenic genes comprises Ox40, GITR, 4-1BB, CD2, CD28, ICOS, CD27, HVEM, SLAM, CD226, PD1, CTLA4, LAG3, TIM3, B7-H1, PD-L1, TLT-2, CD30, CD160, BTLA, LAIR1, 2B4, CD244, TCR, PD-1, CTLA4, LAG-3, CCR5, PCSK9, APOC3, TRAC, TRBC, or any combination thereof. In some embodiments, the engineered cell comprises one or more tolerogenic factors. In some embodiments, the one or more tolerogenic factors comprises HLA-C, HLA-E, HLA-F, HLA-G, PD-L1, CTLA-4-Ig, CD47, CI-inhibitor, and IL-35, HLA-A, HLA-B, HLA-C, or any combination thereof.

In another aspect, the present disclosure provides a method of making an engineered cell herein, wherein the method comprises delivering to a hematopoietic stem cell (HSC) a gene editing system modifying one or more genes in the HSC.

In some embodiments, the gene editing system is a CRISPR-Cas system. In some embodiments, the CRISPR-Cas system comprises a CRISPR system guide or a polynucleotide encoding the guide, a CRISPR protein or a polynucleotide encoding the CRISPR protein, and optionally a template or a polynucleotide encoding the template, wherein the guide directs sequence specific binding of a CRISPR complex to a target sequence in a genomic locus of the HSC, wherein the template comprises a nucleic acid sequence capable of modifying the target sequence, and whereby the target sequence of the HSC is modified. In some embodiments, the target sequence comprises a protein encoding sequence of the HSC. In some embodiments, the target sequence comprises a regulatory sequence of the HSC. In another aspect, the present disclosure provides a method of treating a disease or disorder of the CNS in a subject, which comprises administering to the subject the composition herein. In some embodiments, the composition is delivered intravascularly or intrathecally. In some embodiments, the composition is delivered to the cerebrospinal fluid (CSF) of the subject. In some embodiments, the composition comprises a syngeneic cell. In some embodiments, the composition comprises an allogeneic cell.

These and other aspects, objects, features, and advantages of the example embodiments will become apparent to those having ordinary skill in the art upon consideration of the following detailed description of illustrated example embodiments.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, $2^{nd}$ edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011).

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically disclosed.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, and cell cultures from bodily fluids. Bodily fluids may be obtained from a mammal organism, for example, by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells, and their progeny of a biological entity obtained in vivo or cultured in vitro are also encompassed.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

All publications, published patent documents, and patent applications cited herein are hereby incorporated by reference to the same extent as though each individual publication, published patent document, or patent application was specifically and individually indicated as being incorporated by reference.

Overview

Embodiments disclosed herein provide compositions and methods for treating brain diseases. The compositions and methods allow for a variety of microglia-related diseases in a more efficient and patent-specific manner.

In one aspect, the present disclosure provides engineered hematopoietic stem cells (HSCs) designed to infiltrate or engraft in the central nervous system (CNS) of a patient. The cells may differentiate into microglial cells, which ameliorate or treat diseases such as Rett syndrome, schizophrenia, or Hurler's syndrome. In some cases, the HSCs may be taken or derived from a patent with genetic variants related to a disease. The HSCs may then be engineered to correct the genetic variants and administered back to the patient for treating the disease.

In another aspect, the present disclosure provides methods for engineering HSCs. The one or more genes may relate to a disease, control differentiation of the HSC, and/or control engrafting efficiency of the HSC. In certain example embodiments, the one or more genes may be a driver of microglial engraftment. In certain example embodiments, the one or more genes may be an inhibitor of microglial engraftment. In certain example embodiments, the one or more genes may comprise a combination of drivers and inhibitors of microglial engraftment. Examples of such drivers or inhibitors include purines and cytokines, such as GM-CSF, CSF-1, and transforming growth factor TGF-β. In certain embodiments, the HSCs are further edited to correct underlying mutations or other genetic differences in microglial function that are associated with diseases caused by microglial dysfunction.

In another aspect, the present disclosure relates to universal donor HSCs comprising the above edits and for which immunogenic genes have been deleted.

Engineered Cells for Differentiation into Microglial Cells

Provided herein include compositions comprising engineered cells that may (e.g., are designed to) infiltrate or engraft in the central nervous system (CNS) and treat or ameliorate a disease or disorder of the CNS. After infiltration or engraftment, the engineered cells may treat or ameliorate a disease. Alternatively or additionally, after infiltration or engraftment, the engineered cells may (e.g., are designed to) differentiate into a microglial cell.

When used for administration to a subject, the engineered cells may be syngeneic, allogeneic, autogenic, or xenogeneic. In some cases, the cells may be syngeneic. The cells may be from a donor that has one or more genes substantially identical to counterpart gene(s) in the subject. For example, the one or more genes may encode one or more leukocyte antigen proteins (e.g., human leukocyte antigen (HLA) proteins). In some cases, the cells may be allogeneic, e.g., cells from a donor of the same species as the subject. In some cases, the cells may be autogenic, e.g., cells from the subject. In some cases, the cells may be xenogeneic, e.g., cells from a donor of different species from the subject.

The cells herein may be delivered to the brain of a subject. Examples of methods for delivering cells to the brain include those described in Alexander Aleynik et al., Stem cell delivery of therapies for brain disorders, Clin Transl Med. 2014; 3:24; and David Akhavan et al., CAR T cells for brain tumors: Lessons learned and road ahead, Immunol Rev. 2019 July; 290 (1): 60-84. The cells, compositions, systems, drugs or reagents (e.g., growth factors or signaling molecules) or any combination thereof may be delivered to the brain of a subject. Examples of methods for delivery include those described in Bhujbal S V et al., Drug and cell encapsulation: alternative delivery options for the treatment of malignant brain tumors, Adv Drug Deliv Rev. 2014 April; 67-68:142-53; Neal E G, et al., An update on intracerebral stem cell grafts, Expert Rev Neurother. 2018 July; 18 (7): 557-572; Patel M M et al., Getting into the brain: approaches to enhance brain drug delivery, CNS Drugs. 2009; 23 (1): 35-58; Xiaowei Dong, Current Strategies for Brain Drug Delivery, Theranostics. 2018; 8 (6): 1481-1493.

Microglial Cells

In some examples, the engineered cells comprise or are capable of differentiating into microglial cells. Microglial cells may comprise immune effector cells in the central nervous system. In certain cases, microglial cells may be progeny of HSCs. In some examples, when administered into a subject (e.g., injected intravascularly or intraventricularly), HSCs may differentiate into microglial cells (see, e.g., Capotondo et al., Science Advances, Vol. 3, No. 12, e1701211, Dec. 6, 2017). Examples of microglial cells include amoeboid microglia, ramified microglia, and reactive microglia that respond to injury or pathogen invasion. Microglia can be identified through their expression of characteristic markers including, but not limited, to CD11b and CD45low, Iba1, F4/80, CD68, HLA-DR, transmembrane protein 119 (Tmem119), and CD40 (see, e.g., Korzhevskii, D. E. and Kirik, O. V. Neuroscience and Behavioral Physiology 46 (3): 284-90 (2016); Bennet, M. L. et al., Proc. Nat. Acad. Sci. U.S.A. 113 (12): E1738-40 (2016)). Methods of differentiating induced pluripotent stem cells to microglia-like cells through sequential differentiation have been described (see, e.g., Pandya, H. et al., Nature Neurosci., 20 (5): 753-59 (2017)).

Stem Cells

In some embodiments, the engineered cells designed to infiltrate or engraft the CNS and differentiate into microglial cells may comprise stem cells. Alternatively or additionally, the engineered cells may comprise one or more types of progeny cells of stem cells. As used herein, the term "stem cell" refers to a master cell that can differentiate to form the specialized cells of tissues and organs. A stem cell is a developmentally pluripotent or multipotent cell. A stem cell can divide to produce two daughter stem cells, or one daughter stem cell and one progenitor ("transit") cell, which then proliferates into the tissue's mature, fully formed cells.

The stem cells may be embryonic stem cells, induced pluripotent stem cells, somatic stem cells, or any combination thereof. The term "embryonic stem (ES) cells" refers to pluripotent stem cells derived from embryos. The term "somatic stem cell refers to any pluripotent or multipotent stem cell derived from non-embryonic tissue, including fetal, juvenile, and adult tissue. Natural somatic stem cells have been isolated from a wide variety of adult tissues including blood, bone marrow, brain, olfactory epithelium, skin, pancreas, skeletal muscle, and cardiac muscle. Each of these somatic stem cells can be characterized based on gene expression, factor responsiveness, and morphology in culture. Exemplary naturally occurring somatic stem cells include, but are not limited to, neural stem cells, neural crest stem cells, mesenchymal stem cells, hematopoietic stem cells, and pancreatic stem cells, epithelial stem cells, and muscle satellite cells.

In some examples, the stem cells are iPS cells. The term "induced pluripotent stem cell" (or "iPS cell") refers to a stem cell induced from a somatic cell, e.g., a differentiated somatic cell, and that has a higher potency than said somatic cell. iPS cells are capable of self-renewal and differentiation into mature cells. An iPS cell may be an artificially derived stem cell from a non-pluripotent cell, typically an adult somatic cell, produced by inducing expression of one or more reprogramming genes or corresponding proteins or RNAs. Such stem cell specific genes include, but are not limited to, the family of octamer transcription factors, e.g., Oct-3/4; the family of Sox genes, i.e. Sox1, Sox2, Sox3, Sox 15 and Sox 18; the family of Klf genes, i.e. Klf1, Klf2, Klf4 and Klf5; the family of Myc genes, i.e. c-myc and L-myc; the family of Nanog genes, i.e. OCT4, NANOG and REX1; or LIN28. Examples of iPSCs and methods of preparing them are described in Takahashi et al. (2007) Cell 131 (5): 861-72; Takahashi & Yamanaka (2006) Cell 126:663-76; Okita et al. (2007) Nature 448:260-262; Yu et al. (2007) Science 318 (5858): 1917-20; and Nakagawa et al. (2008) Nat. Biotechnol. 26 (1): 101-6.

In certain example embodiments, the stem cells as defined above are capable of differentiating into a microglial either prior to, or following engraftment into the CNS.

Hematopoietic Stem Cells

In some embodiments, the stem cells capable of infiltrating or engrafting in the CNS and differentiating into microglial cells may be hematopoietic stem and progenitor cells (HSPCs). The term "Hematopoietic Stem Cell and Progenitor Cells", or "HSPC" as used herein, is meant to include broadly those cells considered to be an HSC, e.g., blood cells that give rise to all the other blood cells and are derived from mesoderm, located in the red bone marrow, which is contained in the core of most bones. HSCs used herein may include cells having a phenotype of hematopoietic stem cells, identified by small size, lack of lineage (lin) markers, and markers that belong to the cluster of differentiation series, for example, CD34, CD38, CD90, CD133, CD105, CD45, and also c-kit, —the receptor for stem cell factor. Hematopoietic stem cells may be negative for the markers that are used for detection of lineage commitment and are thus called Lin−; and, during their purification by FACS, a number of up to 14 different mature blood-lineage markers, e.g., CD13 and CD33 for myeloid, CD71 for erythroid, CD19 for B cells, CD61 for megakaryocytic, etc. for humans; and, B220 (murine CD45) for B cells, Mac-1 (CD11b/CD18) for monocytes, Gr-1 for Granulocytes, Ter119 for erythroid cells, Il7Ra, CD3, CD4, CD5, CD8 for T cells, etc. Mouse HSC markers: CD34lo/−, SCA-1+, Thy1.1+/lo, CD38+, C-kit+, lin−, and Human HSC markers: CD34+, CD59+, Thy1/CD90+, CD38lo/−, C-kit/CD117+, and lin− may be used. HSCs may be identified by markers. Hence in embodiments discussed herein, the HSCs may be CD34+ cells. HSCs may also be hematopoietic stem cells that are CD34−/CD38−. Stem cells that may lack c-kit on the cell surface that are considered in the art as HSCs are within the ambit of the disclosure, as well as CD133+ cells likewise considered HSCs in the art.

In some examples, the engineered cells (e.g., HSCs or engineered HSCs) herein include donor cells (e.g., donor HSCs) in which one or more immunogenic genes are modified (e.g., as compared to a wild type counterpart cell). In some cases, such donor cells (e.g., donor HSCs) may have one or more genes whose expression is suppressed (e.g., the one or more genes are deleted). Examples of genes that can be deleted include Ox40, GITR, 4-1BB, CD2, CD28, ICOS, CD27, HVEM, SLAM, CD226, PD1, CTLA4, LAG3, TIM3, B7-H1, PD-L1, TLT-2, CD30, CD160, BTLA, LAIR1, 2B4, CD244, TCR, PD-1, CTLA4, LAG-3, CCR5, PCSK9, APOC3, TRAC, TRBC, and any combination thereof. Alternatively or additionally, the donor cells (e.g., donor HSCs) may express one or more tolerogenic factors, e.g., HLA-C, HLA-E, HLA-F, HLA-G, PD-L1, CTLA-4-Ig, CD47, CI-inhibitor, and IL-35, HLA-A, HLA-B, HLA-C, or any combination thereof. The one or more tolerogenic factors may be expressed in the donor cells using exogenous nucleic acids.

HSC Progeny Cells

In some embodiments, the engineered cells designed to infiltrate or engraft in the CNS may comprise or are capable of differentiating to one or more type of HSC progeny cells. The progeny cells may be used for treating or ameliorating a disease. Examples of HSC progeny cells include cells of the myeloid and lymphoid lineages of blood, including T cells, B cells, monocytes, macrophages, neutrophils, basophils, eosinophils, erythrocytes, dendritic cells, granulocytes, osteoclasts, antigen-presenting cells, and megakaryocytes or platelets, and natural killer cells and their precursors and progenitors. In one example embodiment, the HSC progeny cell may be a short-term hematopoietic stem cell (ST-HSC), a multipotential progenitor cell (MPP), a common myeloid progenitor cell (CMP), a colony-forming unit-granulocyte/erythrocyte/macrophage/megakaryocyte cell (CFU-GEMM); a colony-forming unit-granulocyte/macrophage (CFU-GM), a colony-forming unit-macrophage (CFU-M), a monoblast, and/or a monocyte.

Engraftment

The engineered cells may be capable of engrafting or infiltrating in a tissue or organ, such as a nervous system (e.g., CNS). For example, the engineered cells may be capable of engrafting in the brain or spinal cord. Engraftment refers to the ability of the engineered cells (e.g., engineered hematopoietic stem) and progeny cells to repopulate a tissue, whether such cells are naturally circulating or are provided by transplantation. The term encompasses all events surrounding or leading up to engraftment, such as tissue homing of cells and colonization of cells within the tissue of interest. The engraftment efficiency or rate of engraftment can be evaluated or quantified using any clinically acceptable parameter as known to those of skill in the art and can include, for example, assessment of competitive repopulating units (CRU); incorporation or expression of a marker in tissue(s) into which stem cells have homed, colonized, or become engrafted; or by evaluation of the progress of a subject through disease progression, survival of hematopoietic stem and progenitor cells, or survival of a recipient. Engraftment can also be determined by measuring white blood cell counts in peripheral blood during a post-transplant period. Engraftment can also be assessed by measuring recovery of marrow cells by donor cells in a bone marrow aspirate sample.

In some embodiments, the engineered cells may comprise one or more genes that regulate engraftment efficiency. The terms "engraftment efficiency" is used herein to mean any effects resulting in the ability of stem cells to repopulate a tissue, whether such cells are naturally circulating or are provided by transplantation. The term encompasses all events surrounding or leading up to engraftment, such as tissue homing of cells and colonization of cells within the tissue of interest. The engraftment efficiency can be evaluated or quantified using any clinically acceptable parameter, for example, by assessment of competitive repopulating units (CRU); incorporation or expression of a marker in tissue(s) into which stem cells have homed, colonized, or become engrafted; or by evaluation of the progress of a subject through disease progression, survival of stem cells, or survival of a recipient. In some examples, the engineered cells may comprise or be depleted of one or more genes that enhance engraftment efficiency. For example, the engineered cells may be depleted of CD26 and/or stromal cell-derived factor-1.

Methods of Making Engineered Cells

The present disclosure further includes methods for making engineered cells, e.g., the engineered cells described herein. In general, the methods may include delivering to a cell a composition for engineering the cell. In embodiments, the methods may comprise modulating the expression and/or function of one or more target genes involved in the differentiation of a progenitor cells (e.g., stem cells) into microglial cells. Examples of target genes include IBA1, CD11b, CD45, CD68, TMEM119, P2RY12, TREM2, SLCO2B1, GPR34, P2RY12, P2RY13, ENTPD1, BLNK, RAB3IL1, ADORA3, CRYBB1, GAL3ST4, and any combinations thereof. Additionally or alternatively, the cells (e.g., the progenitor cells) may be exposed to one or more agents that regulate the expression and/or functions of one or more target genes and related signaling pathways. Examples of such agents include NGD, CSF1, IL-34, hVEGF, hBMP4, hSCF and hActivin A, hSCF, hFlt3L, hIL-3, hIL-6, hG-CSF, hBMP4, or a combination thereof. Examples of the target genes, agents, and related methods include those described in Zheng W et al., Differentiation of Glial Cells From hiPSCs: Potential Applications in Neurological Diseases and Cell Replacement Therapy, Front Cell Neurosci. 2018 Aug. 8; 12:239; Douvaras P, et al., Directed Differentiation of Human Pluripotent Stem Cells to Microglia., Stem Cell Reports. 2017 Jun. 6; 8 (6): 1516-1524; Pandya H, Differentiation of human and murine induced pluripotent stem cells to microglia-like cells, Nat Neurosci. 2017 May; 20 (5): 753-759; Martin A. Eglitis et al., Hematopoietic cells differentiate into both microglia and macroglia in the brains of adult mice, Proc Natl Acad Sci USA. 1997 Apr. 15; 94 (8): 4080-4085; Vitry S, et al., Primordial hematopoietic stem cells generate microglia but not myelin-forming cells in a neural environment, J Neurosci. 2003 Nov. 19; 23 (33): 10724-31; Pocock J M et al., Modelling microglial function with induced pluripotent stem cells: an update, Nat Rev Neurosci. 2018 August; 19 (8): 445-452. The differentiation process and related pathways may be monitored when making the engineered cells. Examples of the monitoring methods include those described in Miura T, et al., Monitoring early differentiation events in human embryonic stem cells by massively parallel signature sequencing and expressed sequence tag scan, Stem Cells Dev. 2004 December; 13 (6): 694-715; Masahiro Yasunaga, et a., Induction and monitoring of definitive and visceral endoderm differentiation of mouse ES cells, Nature Biotechnology volume 23, pages 1542-1550 (2005). Examples of monitoring methods also include those described in WO2019060450A1 (e.g., paragraphs [196]-[210]), which is incorporated by reference herein in its entirety.

Gene Editing Systems

Methods of making the engineered cells may comprise delivering to a gene editing systems or components thereof to one or more cells. The gene editing system may modulate the (e.g., activate or suppress) the expression and/or function of one or more target genes involved in the differentiation of stem cells into microglial cells.

The gene editing system may be a CRISPR-Cas system, a Zinc finger nuclease system, a Transcription Activator-like Effector nuclease (TALEN) system, or a meganuclease system.

Talens

In certain embodiments, the gene editing system is a TALEN system. For example, the TALEN system may comprise a transcription activator-like effector nuclease (TALEN), a engineered variant thereof, or nucleic acids encoding thereof. Transcription activator-like effectors (TALEs) can be engineered to bind practically any desired DNA sequence. Exemplary methods of genome editing using the TALEN system can be found for example in Cermak T. Doyle E L. Christian M. Wang L. Zhang Y. Schmidt C, et al. Efficient design and assembly of custom TALEN and other TAL effector-based constructs for DNA targeting. Nucleic Acids Res. 2011; 39: e82; Zhang F. Cong L. Lodato S. Kosuri S. Church G M. Arlotta P Efficient construction of sequence-specific TAL effectors for modulating mammalian transcription. Nat Biotechnol. 2011; 29:149-153, and U.S. Pat. Nos. 8,450,471, 8,440,431 and 8,440,432, all of which are specifically incorporated herein by reference. By means of further guidance, and without limitation, naturally occurring TALEs or "wild type TALEs" are nucleic acid binding proteins secreted by numerous species of proteobacteria. TALE polypeptides contain a nucleic acid binding domain composed of tandem repeats of highly conserved monomer polypeptides that are predominantly 33, 34 or 35 amino acids in length and that differ from each other mainly in amino acid positions 12 and 13. In advantageous embodiments, the nucleic acid is DNA. As used herein, the term "polypeptide monomers", or "TALE monomers" will be used to refer to the highly conserved repetitive polypeptide sequences within the TALE nucleic acid binding domain and the term "repeat variable diresidues" or "RVD" will be used to refer to the highly variable amino acids at positions 12 and 13 of the polypeptide monomers. As provided throughout the disclosure, the amino acid residues of the RVD are depicted using the IUPAC single letter code for amino acids. A general representation of a TALE monomer which is comprised within the DNA binding domain is X1-11-(X12X13)-X14-33 or 34 or 35, where the subscript indicates the amino acid position and X represents any amino acid. X12X13 indicate the RVDs. In some polypeptide monomers, the variable amino acid at position 13 is missing or absent and in such polypeptide monomers, the RVD consists of a single amino acid. In such cases the RVD may be alternatively represented as X*, where X represents X12 and (*) indicates that X13 is absent. The DNA binding domain comprises several repeats of TALE monomers, and this may be represented as (X1-11-(X12X13)-X14-33 or 34 or 35) z, where, in an advantageous embodiment, z is at least 5 to 40. In a further advantageous embodiment, z is at least 10 to 26. The TALE monomers have a nucleotide binding affinity that is determined by the identity of the amino acids in its RVD. For example, polypeptide monomers with an RVD of NI preferentially bind to adenine (A), polypeptide monomers with an RVD of NG preferentially bind to thymine (T), polypeptide monomers with an RVD of HD preferentially bind to cytosine (C), and polypeptide monomers with an RVD of NN preferentially bind to both adenine (A) and guanine (G). In yet another embodiment of the invention, polypeptide monomers with an RVD of IG preferentially bind to T. Thus, the number and order of the polypeptide monomer repeats in the nucleic acid binding domain of a TALE determines its nucleic acid target specificity. In still further embodiments of the invention, polypeptide monomers with an RVD of NS recognize all four base pairs and may bind to A, T, G or C. The structure and function of TALEs is further described in, for example, Moscou et al., Science 326:1501 (2009); Boch et al., Science 326:1509-1512 (2009); and Zhang et al., Nature Biotechnology 29:149-153 (2011), each of which is incorporated by reference in its entirety. In certain embodiments, targeting is affected by a polynucleic acid binding TALEN fragment. In certain embodiments, the targeting domain comprises or consists of a catalytically inactive TALEN or nucleic acid binding fragment thereof.

Zn-Finger Nucleases

In certain embodiments, the gene editing system is a ZFN system. For example, the ZFN system may comprise a zinc-finger nuclease, an engineered variant thereof, or nucleic acid encoding thereof. The ZFN system may use artificial restriction enzymes generated by fusing a zinc finger DNA-binding domain to a DNA-cleavage domain that can be engineered to target desired DNA sequences. Exemplary methods of genome editing using ZFNs can be found for example in U.S. Pat. Nos. 6,534,261, 6,607,882, 6,746, 838, 6,794,136, 6,824,978, 6,866,997, 6,933,113, 6,979,539, 7,013,219, 7,030,215, 7,220,719, 7,241,573, 7,241,574, 7,585,849, 7,595,376, 6,903,185, and 6,479,626, all of which are specifically incorporated herein by reference. By means of further guidance, and without limitation, artificial zinc-finger (ZF) technology may involve arrays of ZF modules to target new DNA-binding sites in the genome. Each finger module in a ZF array targets three DNA bases. A customized array of individual zinc finger domains is assembled into a ZF protein (ZFP). ZFPs can comprise a functional domain. The first synthetic zinc finger nucleases (ZFNs) were developed by fusing a ZF protein to the catalytic domain of the Type IIS restriction enzyme FokI. (Kim, Y. G. et al., 1994, Chimeric restriction endonuclease, Proc. Natl. Acad. Sci. U.S.A. 91, 883-887; Kim, Y. G. et al., 1996, Hybrid restriction enzymes: zinc finger fusions to Fok I cleavage domain. Proc. Natl. Acad. Sci. U.S.A. 93, 1156-1160). Increased cleavage specificity can be attained with decreased off-target activity by use of paired ZFN heterodimers, each targeting different nucleotide sequences separated by a short spacer. (Doyon, Y. et al., 2011, Enhancing zinc-finger-nuclease activity with improved obligate heterodimeric architectures. Nat. Methods 8, 74-79). ZFPs can also be designed as transcription activators and repressors and have been used to target many genes in a wide variety of organisms. In certain embodiments, the targeting domain comprises or consists of a nucleic acid binding zinc finger nuclease or a nucleic acid binding fragment thereof. In certain embodiments, the nucleic acid binding (fragment of) a zinc finger nuclease is catalytically inactive.

Meganuclease

In certain embodiments, the gene editing system is a meganuclease system. For example, the meganuclease system may comprise a meganuclease, a engineered variant thereof, or nucleic acids encoding thereof. The meganuclease may be endodeoxyribonucleases characterized by a large recognition site (double-stranded DNA sequences of 12 to 40 base pairs). An exemplary method for using meganucleases can be found in U.S. Pat. Nos. 8,163,514, 8,133,697, 8,021,867, 8,119,361, 8,119,381, 8,124,369, and 8,129,134, which are specifically incorporated herein by reference. In certain embodiments, targeting is affected by a polynucleic acid binding meganuclease fragment. In certain embodiments, targeting is affected by a polynucleic acid binding catalytically inactive meganuclease (fragment). Accordingly, in particular embodiments, the targeting domain comprises or consists of a nucleic acid binding meganuclease or a nucleic acid binding fragment thereof.

CRISPR-Cas Systems

In some embodiments, the gene editing system may be a CRISPR-Cas system. A CRISPR-Cas system may comprise a CRISPR system guide or a polynucleotide encoding the guide. The guide may direct sequence-specific binding of a CRISPR complex to a target sequence in a genomic locus of the cell to be engineered. The targeted sequence may be modified by the CRISPR-Cas system. Alternatively or additionally, CRISPR-Cas system may comprise a CRISPR-Cas protein or a polynucleotide encoding the CRISPR protein. In some cases, a CRISPR-Cas system may further comprise a template or a polynucleotide encoding the template. The template may comprise a nucleic acid sequence capable of modifying the target sequence.

In some embodiments, one or more genes can be modified using a CRISPR-Cas and/or Cas-based system. In general, a CRISPR-Cas or CRISPR system as used herein and in other documents, such as WO 2014/093622 (PCT/US2013/074667), refers collectively to transcripts and other elements involved in the expression of or directing the activity of CRISPR-associated ("Cas") genes, including sequences encoding a Cas gene, a tracr (trans-activating CRISPR) sequence (e.g., tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas, such as Cas9, e.g., CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). See, e.g., Shmakov et al. (2015) "Discovery and Functional Characterization of Diverse Class 2 CRISPR-Cas Systems", Molecular Cell, DOI: dx.doi.org/10.1016/j.molcel.2015.10.008.

CRISPR-Cas systems can generally fall into two classes based on their architectures of their effector molecules, which are each further subdivided by type and subtype. The two class are Class 1 and Class 2. Class 1 CRISPR-Cas systems have effector modules composed of multiple Cas proteins, some of which form crRNA-binding complexes, while Class 2 CRISPR-Cas systems include a single, multi-domain crRNA-binding protein.

In some embodiments, the CRISPR-Cas system that can be used to modify a polynucleotide of the present invention described herein can be a Class 1 CRISPR-Cas system. In some embodiments, the CRISPR-Cas system that can be used to modify a polynucleotide of the present invention described herein can be a Class 2 CRISPR-Cas system.

Class 1 CRISPR-Cas Systems

In some embodiments, the CRISPR-Cas system that can be used to modify a polynucleotide of the present invention described herein can be a Class 1 CRISPR-Cas system. Class 1 CRISPR-Cas systems are divided into types I, II, and IV. Makarova et al. 2020. Nat. Rev. 18:67-83., particularly as described in Figure 1. Type I CRISPR-Cas systems are divided into 9 subtypes (I-A, I-B, I-C, I-D, I-E, I-F1, I-F2, I-F3, and IG). Makarova et al., 2020. Class 1, Type I CRISPR-Cas systems can contain a Cas3 protein that can have helicase activity. Type III CRISPR-Cas systems are divided into 6 subtypes (III-A, III-B, III-C, III-D, III-E, and III-F). Type III CRISPR-Cas systems can contain a Cas10 that can include an RNA recognition motif called Palm and a cyclase domain that can cleave polynucleotides. Makarova et al., 2020. Type IV CRISPR-Cas systems are divided into 3 subtypes. (IV-A, IV-B, and IV-C) . . . . Makarova et al., 2020. Class 1 systems also include CRISPR-Cas variants, including Type I-A, I-B, I-E, I-F and I-U variants, which can include variants carried by transposons and plasmids, including versions of subtype I-F encoded by a large family of Tn7-like transposon and smaller groups of Tn7-like transposons that encode similarly degraded subtype I-B systems. Peters et al., PNAS 114 (35) (2017); DOI: 10.1073/pnas.1709035114; see also, Makarova et al. 2018. The CRISPR Journal, v. 1, n5, Figure 5.

The Class 1 systems typically use a multi-protein effector complex, which can, in some embodiments, include ancillary proteins, such as one or more proteins in a complex referred to as a CRISPR-associated complex for antiviral defense (Cascade), one or more adaptation proteins (e.g., Cas1, Cas2, RNA nuclease), and/or one or more accessory proteins (e.g., Cas 4, DNA nuclease), CRISPR associated Rossman fold (CARF) domain containing proteins, and/or RNA transcriptase.

The backbone of the Class 1 CRISPR-Cas system effector complexes can be formed by RNA recognition motif domain-containing protein(s) of the repeat-associated mysterious proteins (RAMPs) family subunits (e.g., Cas 5, Cas6, and/or Cas7). RAMP proteins are characterized by having one or more RNA recognition motif domains. In some embodiments, multiple copies of RAMPs can be present. In some embodiments, the Class I CRISPR-Cas system can include 1, 2, 3, 4, 5, 6, 7, 8, 9, 10, 11, 12 or more Cas5, Cas6, and/or Cas 7 proteins. In some embodiments, the Cas6 protein is an RNAse, which can be responsible for precrRNA processing. When present in a Class 1 CRISPR-Cas system, Cas6 can be optionally physically associated with the effector complex.

Class 1 CRISPR-Cas system effector complexes can, in some embodiments, also include a large subunit. The large subunit can be composed of or include a Cas8 and/or Cas10 protein. See, e.g., Figures 1 and 2. Koonin E V, Makarova K S. 2019. Phil. Trans. R. Soc. B 374:20180087, DOI: 10.1098/rstb.2018.0087 and Makarova et al. 2020.

Class 1 CRISPR-Cas system effector complexes can, in some embodiments, include a small subunit (for example, Cas11). See, e.g., Figures 1 and 2. Koonin E V, Makarova K S. 2019 Origins and Evolution of CRISPR-Cas systems. Phil. Trans. R. Soc. B 374:20180087, DOI: 10.1098/rstb.2018.0087.

In some embodiments, the Class 1 CRISPR-Cas system can be a Type I CRISPR-Cas system. In some embodiments, the Type I CRISPR-Cas system can be a subtype I-A CRISPR-Cas system. In some embodiments, the Type I CRISPR-Cas system can be a subtype I-B CRISPR-Cas system. In some embodiments, the Type I CRISPR-Cas system can be a subtype I-C CRISPR-Cas system. In some embodiments, the Type I CRISPR-Cas system can be a subtype I-D CRISPR-Cas system. In some embodiments, the Type I CRISPR-Cas system can be a subtype I-E CRISPR-Cas system. In some embodiments, the Type I CRISPR-Cas system can be a subtype I-F1 CRISPR-Cas system. In some embodiments, the Type I CRISPR-Cas system can be a subtype I-F2 CRISPR-Cas system. In some embodiments, the Type I CRISPR-Cas system can be a subtype I-F3 CRISPR-Cas system. In some embodiments, the Type I CRISPR-Cas system can be a subtype I-G CRISPR-Cas system. In some embodiments, the Type I CRISPR-Cas system can be a CRISPR Cas variant, such as a Type I-A, I-B, I-E, I-F and I-U variants, which can include variants carried by transposons and plasmids, including versions of subtype I-F encoded by a large family of Tn7-like transposon and smaller groups of Tn7-like transposons that encode similarly degraded subtype I-B systems as previously described.

In some embodiments, the Class 1 CRISPR-Cas system can be a Type III CRISPR-Cas system. In some embodiments, the Type III CRISPR-Cas system can be a subtype III-A CRISPR-Cas system. In some embodiments, the Type III CRISPR-Cas system can be a subtype III-B CRISPR-Cas system. In some embodiments, the Type III CRISPR-Cas system can be a subtype III-C CRISPR-Cas system. In some embodiments, the Type III CRISPR-Cas system can be a subtype III-D CRISPR-Cas system. In some embodiments, the Type III CRISPR-Cas system can be a subtype III-E CRISPR-Cas system. In some embodiments, the Type III CRISPR-Cas system can be a subtype III-F CRISPR-Cas system.

In some embodiments, the Class 1 CRISPR-Cas system can be a Type IV CRISPR-Cas-system. In some embodiments, the Type IV CRISPR-Cas system can be a subtype IV-A CRISPR-Cas system. In some embodiments, the Type IV CRISPR-Cas system can be a subtype IV-B CRISPR-Cas system. In some embodiments, the Type IV CRISPR-Cas system can be a subtype IV-C CRISPR-Cas system.

The effector complex of a Class 1 CRISPR-Cas system can, in some embodiments, include a Cas3 protein that is optionally fused to a Cas2 protein, a Cas4, a Cas5, a Cas6, a Cas7, a Cas8, a Cas10, a Cas11, or a combination thereof. In some embodiments, the effector complex of a Class 1 CRISPR-Cas system can have multiple copies, such as 1, 2, 3, 4, 5, 6, 7, 8, 9, 10, 11, 12, 13, or 14, of any one or more Cas proteins.

Class 2 CRISPR-Cas Systems

The compositions, systems, and methods described in greater detail elsewhere herein can be designed and adapted for use with Class 2 CRISPR-Cas systems. Thus, in some embodiments, the CRISPR-Cas system is a Class 2 CRISPR-Cas system. Class 2 systems are distinguished from Class 1 systems in that they have a single, large, multi-domain effector protein. In certain example embodiments, the Class 2 system can be a Type II, Type V, or Type VI system, which are described in Makarova et al. "Evolutionary classification of CRISPR-Cas systems: a burst of class 2 and derived variants" Nature Reviews Microbiology, 18:67-81 (February 2020), incorporated herein by reference. Each type of Class 2 system is further divided into subtypes. See Markova et al. 2020, particularly at Figure. 2. Class 2, Type II systems can be divided into 4 subtypes: II-A, II-B, II-C1, and II-C2. Class 2, Type V systems can be divided into 17 subtypes: V-A, V-B1, V-B2, V-C, V-D, V-E, V-F1, V-F1 (V-U3), V-F2, V-F3, V-G, V-H, V-I, V-K (V-U5), V-U1, V-U2, and V-U4. Class 2, Type IV systems can be divided into 5 subtypes: VI-A, VI-B1, VI-B2, VI-C, and VI-D.

The distinguishing feature of these types is that their effector complexes consist of a single, large, multi-domain protein. Type V systems differ from Type II effectors (e.g., Cas9), which contain two nuclear domains that are each responsible for the cleavage of one strand of the target DNA, with the HNH nuclease inserted inside the Ruv-C like nuclease domain sequence. The Type V systems (e.g., Cas12) only contain a RuvC-like nuclease domain that cleaves both strands. Type VI (Cas13) are unrelated to the effectors of Type II and V systems and contain two HEPN domains and target RNA. Cas13 proteins also display collateral activity that is triggered by target recognition. Some Type V systems have also been found to possess this collateral activity with two single-stranded DNA in in vitro contexts.

In some embodiments, the Class 2 system is a Type II system. In some embodiments, the Type II CRISPR-Cas system is a II-A CRISPR-Cas system. In some embodiments, the Type II CRISPR-Cas system is a II-B CRISPR-Cas system. In some embodiments, the Type II CRISPR-Cas system is a II-C1 CRISPR-Cas system. In some embodiments, the Type II CRISPR-Cas system is a II-C2 CRISPR-Cas system. In some embodiments, the Type II system is a Cas9 system. In some embodiments, the Type II system includes a Cas9.

In some embodiments, the Class 2 system is a Type V system. In some embodiments, the Type V CRISPR-Cas system is a V-A CRISPR-Cas system. In some embodiments, the Type V CRISPR-Cas system is a V-B1 CRISPR-Cas system. In some embodiments, the Type V CRISPR-Cas system is a V-B2 CRISPR-Cas system. In some embodiments, the Type V CRISPR-Cas system is a V-C CRISPR-Cas system. In some embodiments, the Type V CRISPR-Cas system is a V-D CRISPR-Cas system. In some embodiments, the Type V CRISPR-Cas system is a V-E CRISPR-Cas system. In some embodiments, the Type V CRISPR-Cas system is a V-F1 CRISPR-Cas system. In some embodiments, the Type V CRISPR-Cas system is a V-F1 (V-U3) CRISPR-Cas system. In some embodiments, the Type V CRISPR-Cas system is a V-F2 CRISPR-Cas system. In some embodiments, the Type V CRISPR-Cas system is a V-F3 CRISPR-Cas system. In some embodiments, the Type V CRISPR-Cas system is a V-G CRISPR-Cas system. In some embodiments, the Type V CRISPR-Cas system is a V-H CRISPR-Cas system. In some embodiments, the Type V CRISPR-Cas system is a V-I CRISPR-Cas system. In some embodiments, the Type V CRISPR-Cas system is a V-K (V-U5) CRISPR-Cas system. In some embodiments, the Type V CRISPR-Cas system is a V-U1 CRISPR-Cas system. In some embodiments, the Type V CRISPR-Cas system is a V-U2 CRISPR-Cas system. In some embodiments, the Type V CRISPR-Cas system is a V-U4 CRISPR-Cas system. In some embodiments, the Type V CRISPR-Cas system includes a Cas12a (Cpf1), Cas12b (C2c1), Cas12c (C2c3), CasX, and/or Cas14.

In some embodiments the Class 2 system is a Type VI system. In some embodiments, the Type VI CRISPR-Cas system is a VI-A CRISPR-Cas system. In some embodiments, the Type VI CRISPR-Cas system is a VI-B1 CRISPR-Cas system. In some embodiments, the Type VI CRISPR-Cas system is a VI-B2 CRISPR-Cas system. In some embodiments, the Type VI CRISPR-Cas system is a VI-C CRISPR-Cas system. In some embodiments, the Type VI CRISPR-Cas system is a VI-D CRISPR-Cas system. In some embodiments, the Type VI CRISPR-Cas system includes a Cas13a (C2c2), Cas13b (Group 29/30), Cas13c, and/or Cas13d.

Specialized Cas-Based Systems

In some embodiments, the system is a Cas-based system that is capable of performing a specialized function or activity. For example, the Cas protein may be fused, operably coupled to, or otherwise associated with one or more functionals domains. In certain example embodiments, the Cas protein may be a catalytically dead Cas protein ("dCas") and/or have nickase activity. A nickase is a Cas protein that cuts only one strand of a double stranded target. In such embodiments, the dCas or nickase provide a sequence specific targeting functionality that delivers the functional domain to or proximate a target sequence. Example functional domains that may be fused to, operably coupled to, or otherwise associated with a Cas protein can be or include, but are not limited to a nuclear localization signal (NLS) domain, a nuclear export signal (NES) domain, a translational activation domain, a transcriptional activation domain (e.g. VP64, p65, MyoD1, HSF1, RTA, and SET7/9), a translation initiation domain, a transcriptional repression domain (e.g., a KRAB domain, NuE domain, NcoR domain, and a SID domain such as a SID4X domain), a nuclease domain (e.g., FokI), a histone modification domain (e.g., a histone acetyltransferase), a light inducible/controllable domain, a chemically inducible/controllable domain, a transposase domain, a homologous recombination machinery domain, a recombinase domain, an integrase domain, and combinations thereof. Methods for generating catalytically dead Cas9 or a nickase Cas9 (WO 2014/204725, Ran et al. Cell. 2013 Sep. 12; 154 (6): 1380-1389), Cas12 (Liu et al. Nature Communications, 8, 2095 (2017), and Cas13 (WO 2019/005884, WO2019/060746) are known in the art and incorporated herein by reference.

In some embodiments, the functional domains can have one or more of the following activities: methylase activity, demethylase activity, translation activation activity, translation initiation activity, translation repression activity, transcription activation activity, transcription repression activity, transcription release factor activity, histone modification activity, nuclease activity, single-strand RNA cleavage activity, double-strand RNA cleavage activity, single-strand DNA cleavage activity, double-strand DNA cleavage activity, molecular switch activity, chemical inducibility, light inducibility, and nucleic acid binding activity. In some embodiments, the one or more functional domains may comprise epitope tags or reporters. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporters include, but are not limited to, glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and auto-fluorescent proteins including blue fluorescent protein (BFP).

The one or more functional domain(s) may be positioned at, near, and/or in proximity to a terminus of the effector protein (e.g., a Cas protein). In embodiments having two or more functional domains, each of the two can be positioned at or near or in proximity to a terminus of the effector protein (e.g., a Cas protein). In some embodiments, such as those where the functional domain is operably coupled to the effector protein, the one or more functional domains can be tethered or linked via a suitable linker (including, but not limited to, GlySer linkers) to the effector protein (e.g., a Cas protein). When there is more than one functional domain, the functional domains can be same or different. In some embodiments, all the functional domains are the same. In some mbodiments, all of the functional domains are different from each other. In some embodiments, at least two of the funcational domains are different from each other. In some embodiments, at least two of the functional domains are the same as each other.

Other suitable functional domains can be found, for example, in International Application Publication No. WO 2019/018423.

Split CRISPR-Cas Systems

In some embodiments, the CRISPR-Cas system is a split CRISPR-Cas system. See e.g., Zetche et al., 2015. Nat. Biotechnol. 33 (2): 139-142 and WO 2019/018423, the compositions and techniques of which can be used in and/or adapted for use with the present invention. Split CRISPR-Cas proteins are set forth herein and in documents incorporated herein by reference in further detail herein. In certain embodiments, each part of a split CRISPR protein are attached to a member of a specific binding pair, and when bound with each other, the members of the specific binding pair maintain the parts of the CRISPR protein in proximity. In certain embodiments, each part of a split CRISPR protein is associated with an inducible binding pair. An inducible binding pair is one which is capable of being switched "on" or "off" by a protein or small molecule that binds to both members of the inducible binding pair. In some embodiments, CRISPR proteins may preferably split between domains, leaving domains intact. In particular embodiments, said Cas split domains (e.g., RuvC and HNH domains in the case of Cas9) can be simultaneously or sequentially introduced into the cell such that said split Cas domain(s) process the target nucleic acid sequence in the algae cell. The reduced size of the split Cas compared to the wild type Cas allows other methods of delivery of the systems to the cells, such as the use of cell penetrating peptides as described herein.

Dna and RNA Base Editing

In some embodiments, a polynucleotide of the present invention described elsewhere herein can be modified using a base editing system. In some embodiments, a Cas protein is connected or fused to a nucleotide deaminase. Thus, in some embodiments the Cas-based system can be a base editing system. As used herein "base editing" refers generally to the process of polynucleotide modification via a CRISPR-Cas-based or Cas-based system that does not include excising nucleotides to make the modification. Base editing can convert base pairs at precise locations without generating excess undesired editing byproducts that can be made using traditional CRISPR-Cas systems.

In certain example embodiments, the nucleotide deaminase may be a DNA base editor used in combination with a DNA binding Cas protein such as, but not limited to, Class 2 Type II and Type V systems. Two classes of DNA base editors are generally known: cytosine base editors (CBEs) and adenine base editors (ABEs). CBEs convert a C·G base pair into a T·A base pair (Komor et al. 2016. Nature. 533:420-424; Nishida et al. 2016. Science. 353; and Li et al. Nat. Biotech. 36:324-327) and ABEs convert an A·T base pair to a G·C base pair. Collectively, CBEs and ABEs can mediate all four possible transition mutations (C to T, A to G, T to C, and G to A). Rees and Liu. 2018. Nat. Rev. Genet. 19 (12): 770-788, particularly at Figures 1b, 2a-2c, 3a-3f, and Table 1. In some embodiments, the base editing system includes a CBE and/or an ABE. In some embodiments, a polynucleotide of the present invention described elsewhere herein can be modified using a base editing system. Rees and Liu. 2018. Nat. Rev. Gent. 19 (12): 770-788. Base editors also generally do not need a DNA donor template and/or rely on homology-directed repair. Komor et al. 2016. Nature. 533:420-424; Nishida et al. 2016. Science. 353; and Gaudeli et al. 2017. Nature. 551:464-471. Upon binding to a target locus in the DNA, base pairing between the guide RNA of the system and the target DNA strand leads to displacement of a small segment of ssDNA in an "R-loop". Nishimasu et al. Cell. 156:935-949. DNA bases within the ssDNA bubble are modified by the enzyme component, such as a deaminase. In some systems, the catalytically disabled Cas protein can be a variant or modified Cas can have nickase functionality and can generate a nick in the non-edited DNA strand to induce cells to repair the non-edited strand using the edited strand as a template. Komor et al. 2016. Nature. 533:420-424; Nishida et al. 2016. Science. 353; and Gaudeli et al. 2017. Nature. 551:464-471.

Other Example Type V base editing systems are described in WO 2018/213708, WO 2018/213726, PCT/US2018/067207, PCT/US2018/067225, and PCT/US2018/067307 which are incorporated by referenced herein.

In certain example embodiments, the base editing system may be a RNA base editing system. As with DNA base editors, a nucleotide deaminase capable of converting nucleotide bases may be fused to a Cas protein. However, in these embodiments, the Cas protein will need to be capable of binding RNA. Example RNA binding Cas proteins include, but are not limited to, RNA-binding Cas9s such as *Francisella novicida* Cas9 ("FnCas9"), and Class 2 Type VI Cas systems. The nucleotide deaminase may be a cytidine deaminase or an adenosine deaminase, or an adenosine deaminase engineered to have cytidine deaminase activity. In certain example embodiments, the RNA based editor may be used to delete or introduce a post-translation modification site in the expressed mRNA. In contrast to DNA base editors, whose edits are permanent in the modified cell, RNA base editors can provide edits where finer temporal control may be needed, for example in modulating a particular immune response. Example Type VI RNA-base editing systems are described in Cox et al. 2017. Science 358:1019-1027, WO 2019/005884, WO 2019/005886, WO 2019/071048, PCT/US20018/05179, PCT/US2018/067207, which are incorporated herein by reference. An example FnCas9 system that may be adapted for RNA base editing purposes is described in WO 2016/106236, which is incorporated herein by reference.

An example method for delivery of base-editing systems, including use of a split-intein approach to divide CBE and ABE into reconstitutable halves, is described in Levy et al. Nature Biomedical Engineering doi.org/10.1038/s41441-019-0505-5 (2019), which is incorporated herein by reference.

Prime Editors

In some embodiments, a polynucleotide of the present invention described elsewhere herein can be modified using a prime editing system See e.g. Anzalone et al. 2019. Nature. 576:149-157. Like base editing systems, prime editing systems can be capable of targeted modification of a polynucleotide without generating double stranded breaks and does not require donor templates. Further prime editing systems can be capable of all 12 possible combination swaps. Prime editing can operate via a "search-and-replace" methodology and can mediate targeted insertions, deletions, all 12 possible base-to-base conversion, and combinations thereof. Generally, a prime editing system, as exemplified by PE1, PE2, and PE3 (Id.), can include a reverse transcriptase fused or otherwise coupled or associated with an RNA-programmable nickase, and a prime-editing extended guide RNA (pegRNA) to facility direct copying of genetic information from the extension on the pegRNA into the target polynucleotide. Embodiments that can be used with the present invention include these and variants thereof. Prime editing can have the advantage of lower off-target activity than traditional CRISPR-Cas systems along with few byproducts and greater or similar efficiency as compared to traditional CRISPR-Cas systems.

In some embodiments, the prime editing guide molecule can specify both the target polynucleotide information (e.g. sequence) and contain a new polynucleotide cargo that replaces target polynucleotides. To initiate transfer from the guide molecule to the target polynucleotide, the PE system can nick the target polynucleotide at a target side to expose a 3'hydroxyl group, which can prime reverse transcription of an edit-encoding extension region of the guide molecule (e.g. a prime editing guide molecule or peg guide molecule) directly into the target site in the target polynucleotide. See e.g. Anzalone et al. 2019. Nature. 576:149-157, particularly at Figures 1b, 1c, related discussion, and supplementary discussion.

In some embodiments, a prime editing system can be composed of a Cas polypeptide having nickase activity, a reverse transcriptase, and a guide molecule. The Cas polypeptide can lack nuclease activity. The guide molecule can include a target binding sequence as well as a primer binding sequence and a template containing the edited polynucleotide sequence. The guide molecule, Cas polypeptide, and/or reverse transcriptase can be coupled together or otherwise associate with each other to form an effector complex and edit a target sequence. In some embodiments, the Cas polypeptide is a Class 2, Type V Cas polypeptide. In some embodiments, the Cas polypeptide is a Cas9 polypeptide (e.g. is a Cas9 nickase). In some embodiments, the Cas polypeptide is fused to the reverse transcriptase. In some embodiments, the Cas polypeptide is linked to the reverse transcriptase.

In some embodiments, the prime editing system can be a PE1 system or variant thereof, a PE2 system or variant thereof, or a PE3 (e.g. PE3, PE3b) system. See e.g., Anzalone et al. 2019. Nature. 576:149-157, particularly at pgs. 2-3, Figures 2a, 3a-3f, 4a-4b, Extended data Figures 3a-3b, 4.

The peg guide molecule can be about 10 to about 200 or more nucleotides in length, such as 10 to/or 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 or more nucleotides in length. Optimization of the peg guide molecule can be accomplished as described in Anzalone et al. 2019. Nature. 576:149-157, particularly at pg. 3, Figure 2a-2b, and Extended Data Figure 5a-c.

CRISPR Associated Transposase (CAST) Systems

In some embodiments, a polynucleotide of the present invention described elsewhere herein can be modified using a CRISPR Associated Transposase ("CAST") system. CAST system can include a Cas protein that is catalytically inactive, or engineered to be catalytically active, and further comprises a transposase (or subunits thereof) that catalyze RNA-guided DNA transposition. Such systems are able to insert DNA sequences at a target site in a DNA molecule without relying on host cell repair machinery. CAST systems can be Class1 or Class 2 CAST systems. An example Class 1 system is described in Klompe et al. Nature, doi: 10.1038/s41586-019-1323, which is in incorporated herein by reference. An example Class 2 system is described in Strecker et al. Science. 10/1126/science. aax9181 (2019), and PCT/US2019/066835 which are incorporated herein by reference.

Guide Molecules

The CRISPR-Cas or Cas-Based system described herein can, in some embodiments, include one or more guide molecules. The terms guide molecule, guide sequence and guide polynucleotide, refer to polynucleotides capable of guiding Cas to a target genomic locus and are used interchangeably as in foregoing cited documents such as WO 2014/093622 (PCT/US2013/074667). In general, a guide sequence is any polynucleotide sequence having sufficient complementarity with a target polynucleotide sequence to hybridize with the target sequence and direct sequence-specific binding of a CRISPR complex to the target sequence. The guide molecule can be a polynucleotide.

The ability of a guide sequence (within a nucleic acid-targeting guide RNA) to direct sequence-specific binding of a nucleic acid-targeting complex to a target nucleic acid sequence may be assessed by any suitable assay. For example, the components of a nucleic acid-targeting CRISPR system sufficient to form a nucleic acid-targeting complex, including the guide sequence to be tested, may be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence, such as by Surveyor assay (Qui et al. 2004. BioTechniques. 36 (4) 702-707). Similarly, cleavage of a target nucleic acid sequence may be evaluated in a test tube by providing the target nucleic acid sequence, components of a nucleic acid-targeting complex, including the guide sequence to be tested and a control guide sequence different from the test guide sequence, and comparing binding or rate of cleavage at the target sequence between the test and control guide sequence reactions. Other assays are possible and will occur to those skilled in the art.

In some embodiments, the guide molecule is an RNA. The guide molecule(s) (also referred to interchangeably herein as guide polynucleotide and guide sequence) that are included in the CRISPR-Cas or Cas based system can be any polynucleotide sequence having sufficient complementarity with a target nucleic acid sequence to hybridize with the target nucleic acid sequence and direct sequence-specific binding of a nucleic acid-targeting complex to the target nucleic acid sequence. In some embodiments, the degree of complementarity, when optimally aligned using a suitable alignment algorithm, can be about or more than about 50%, 60%, 75%, 80%, 85%, 90%, 95%, 97.5%, 99%, or more. Optimal alignment may be determined with the use of any suitable algorithm for aligning sequences, non-limiting examples of which include the Smith-Waterman algorithm, the Needleman-Wunsch algorithm, algorithms based on the Burrows-Wheeler Transform (e.g., the Burrows Wheeler Aligner), Clustal W, Clustal X, BLAT, Novoalign (Novocraft Technologies; available at www.novocraft.com), ELAND (Illumina, San Diego, CA), SOAP (available at soap.genomics.org.cn), and Maq (available at maq.sourceforge.net).

A guide sequence, and hence a nucleic acid-targeting guide may be selected to target any target nucleic acid sequence. The target sequence may be DNA. The target sequence may be any RNA sequence. In some embodiments, the target sequence may be a sequence within an RNA molecule selected from the group consisting of messenger RNA (mRNA), pre-mRNA, ribosomal RNA (rRNA), transfer RNA (tRNA), micro-RNA (miRNA), small interfering RNA (siRNA), small nuclear RNA (snRNA), small nucleolar RNA (snoRNA), double stranded RNA (dsRNA), non-coding RNA (ncRNA), long non-coding RNA (lncRNA), and small cytoplasmatic RNA (scRNA). In some preferred embodiments, the target sequence may be a sequence within an RNA molecule selected from the group consisting of mRNA, pre-mRNA, and rRNA. In some preferred embodiments, the target sequence may be a sequence within an RNA molecule selected from the group consisting of ncRNA, and lncRNA. In some more preferred embodiments, the target sequence may be a sequence within an mRNA molecule or a pre-mRNA molecule.

In some embodiments, a nucleic acid-targeting guide is selected to reduce the degree secondary structure within the nucleic acid-targeting guide. In some embodiments, about or less than about 75%, 50%, 40%, 30%, 25%, 20%, 15%, 10%, 5%, 1%, or fewer of the nucleotides of the nucleic acid-targeting guide participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g., A. R. Gruber et al., 2008, Cell 106 (1): 23-24; and PA Carr and GM Church, 2009, Nature Biotechnology 27 (12): 1151-62).

In certain embodiments, a guide RNA or crRNA may comprise, consist essentially of, or consist of a direct repeat (DR) sequence and a guide sequence or spacer sequence. In certain embodiments, the guide RNA or crRNA may comprise, consist essentially of, or consist of a direct repeat sequence fused or linked to a guide sequence or spacer sequence. In certain embodiments, the direct repeat sequence may be located upstream (i.e., 5') from the guide sequence or spacer sequence. In other embodiments, the direct repeat sequence may be located downstream (i.e., 3') from the guide sequence or spacer sequence.

In certain embodiments, the crRNA comprises a stem loop, preferably a single stem loop. In certain embodiments, the direct repeat sequence forms a stem loop, preferably a single stem loop.

In certain embodiments, the spacer length of the guide RNA is from 15 to 35 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27 to 30 nt, e.g., 27, 28, 29, or 30 nt, from 30 to 35 nt, e.g., 30, 31, 32, 33, 34, or 35 nt, or 35 nt or longer.

The "tracrRNA" sequence or analogous terms includes any polynucleotide sequence that has sufficient complementarity with a crRNA sequence to hybridize. In some embodiments, the degree of complementarity between the tracrRNA sequence and crRNA sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and crRNA sequence are contained within a single transcript, such that hybridization between the two produces a transcript having a secondary structure, such as a hairpin.

In general, degree of complementarity is with reference to the optimal alignment of the sca sequence and tracr sequence, along the length of the shorter of the two sequences. Optimal alignment may be determined by any suitable alignment algorithm, and may further account for secondary structures, such as self-complementarity within either the sca sequence or tracr sequence. In some embodiments, the degree of complementarity between the tracr sequence and sca sequence along the length of the shorter of the two when optimally aligned is about or more than about 25%, 30%, 40%, 50%, 60%, 70%, 80%, 90%, 95%, 97.5%, 99%, or higher.

In some embodiments, the degree of complementarity between a guide sequence and its corresponding target sequence can be about or more than about 50%, 60%, 75%, 80%, 85%, 90%, 95%, 97.5%, 99%, or 100%; a guide or RNA or sgRNA can be about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length; or guide or RNA or sgRNA can be less than about 75, 50, 45, 40, 35, 30, 25, 20, 15, 12, or fewer nucleotides in length; and tracr RNA can be 30 or 50 nucleotides in length. In some embodiments, the degree of complementarity between a guide sequence and its corresponding target sequence is greater than 94.5% or 95% or 95.5% or 96% or 96.5% or 97% or 97.5% or 98% or 98.5% or 99% or 99.5% or 99.9%, or 100%. Off target is less than 100% or 99.9% or 99.5% or 99% or 99% or 98.5% or 98% or 97.5% or 97% or 96.5% or 96% or 95.5% or 95% or 94.5% or 94% or 93% or 92% or 91% or 90% or 89% or 88% or 87% or 86% or 85% or 84% or 83% or 82% or 81% or 80% complementarity between the sequence and the guide, with it advantageous that off target is 100% or 99.9% or 99.5% or 99% or 99% or 98.5% or 98% or 97.5% or 97% or 96.5% or 96% or 95.5% or 95% or 94.5% complementarity between the sequence and the guide.

In some embodiments according to the invention, the guide RNA (capable of guiding Cas to a target locus) may comprise (1) a guide sequence capable of hybridizing to a genomic target locus in the eukaryotic cell; (2) a tracr sequence; and (3) a tracr mate sequence. All (1) to (3) may reside in a single RNA, i.e., an sgRNA (arranged in a 5' to 3' orientation), or the tracr RNA may be a different RNA than the RNA containing the guide and tracr sequence. The tracr hybridizes to the tracr mate sequence and directs the CRISPR/Cas complex to the target sequence. Where the tracr RNA is on a different RNA than the RNA containing the guide and traer sequence, the length of each RNA may be optimized to be shortened from their respective native lengths, and each may be independently chemically modified to protect from degradation by cellular RNase or otherwise increase stability.

Many modifications to guide sequences are known in the art and are further contemplated within the context of this invention. Various modifications may be used to increase the specificity of binding to the target sequence and/or increase the activity of the Cas protein and/or reduce off-target effects. Example guide sequence modifications are described in PCT US2019/045582, specifically paragraphs [0178]-[0333]. which is incorporated herein by reference.

Target Sequences, PAMs, and PFSs

In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise RNA polynucleotides. The term "target RNA" refers to an RNA polynucleotide being or comprising the target sequence. In other words, the target polynucleotide can be a polynucleotide or a part of a polynucleotide to which a part of the guide sequence is designed to have complementarity withand to which the effector function mediated by the complex comprising the CRISPR effector protein and a guide molecule is to be directed. In some embodiments, a target sequence is located in the nucleus or cytoplasm of a cell.

The guide sequence can specifically bind a target sequence in a target polynucleotide. The target polynucleotide may be DNA. The target polynucleotide may be RNA. The target polynucleotide can have one or more (e.g., 1, 2, 3, 4, 5, 6, 7, 8, 9, 10, etc. or more) target sequences. The target polynucleotide can be on a vector. The target polynucleotide can be genomic DNA. The target polynucleotide can be episomal. Other forms of the target polynucleotide are described elsewhere herein.

The target sequence may be DNA. The target sequence may be any RNA sequence. In some embodiments, the target sequence may be a sequence within an RNA molecule selected from the group consisting of messenger RNA (mRNA), pre-mRNA, ribosomal RNA (rRNA), transfer RNA (tRNA), micro-RNA (miRNA), small interfering RNA (siRNA), small nuclear RNA (snRNA), small nucleolar RNA (snoRNA), double stranded RNA (dsRNA), non-coding RNA (ncRNA), long non-coding RNA (lncRNA), and small cytoplasmatic RNA (scRNA). In some preferred embodiments, the target sequence (also referred to herein as a target polynucleotide) may be a sequence within an RNA molecule selected from the group consisting of mRNA, pre-mRNA, and rRNA. In some preferred embodiments, the target sequence may be a sequence within an RNA molecule selected from the group consisting of ncRNA, and lncRNA. In some more preferred embodiments, the target sequence may be a sequence within an mRNA molecule or a pre-mRNA molecule.

PAM and PFS Elements

PAM elements are sequences that can be recognized and bound by Cas proteins. Cas proteins/effector complexes can then unwind the dsDNA at a position adjacent to the PAM element. It will be appreciated that Cas proteins and systems that include them that target RNA do not require PAM sequences (Marraffini et al. 2010. Nature. 463:568-571). Instead, many rely on PFSs, which are discussed elsewhere herein. In certain embodiments, the target sequence should be associated with a PAM (protospacer adjacent motif) or PFS (protospacer flanking sequence or site), that is, a short sequence recognized by the CRISPR complex. Depending on the nature of the CRISPR-Cas protein, the target sequence should be selected, such that its complementary sequence in the DNA duplex (also referred to herein as the non-target sequence) is upstream or downstream of the PAM. In the embodiments, the complementary sequence of the target sequence is downstream or 3' of the PAM or upstream or 5' of the PAM. The precise sequence and length requirements for the PAM differ depending on the Cas protein used, but PAMs are typically 2-5 base pair sequences adjacent the protospacer (that is, the target sequence). Examples of the natural PAM sequences for different Cas proteins are provided herein below and the skilled person will be able to identify further PAM sequences for use with a given Cas protein.

The ability to recognize different PAM sequences depends on the Cas polypeptide(s) included in the system. See e.g., Gleditzsch et al. 2019. RNA Biology. 16 (4): 504-517. Table 3 below shows several Cas polypeptides and the PAM sequence they recognize.

TABLE 3

Example PAM Sequences

| Cas Protein | PAM Sequence |
| --- | --- |
| SpCas9 | NGG/NRG |
| SaCas9 | NGRRT or NGRRN |
| NmeCas9 | NNNNGATT |
| CjCas9 | NNNNRYAC |
| StCas9 | NNAGAAW |
| Cas12a (Cpf1) (including LbCpf1 and AsCpf1) | TTTV |
| Cas12b (C2c1) | TTT, TTA, and TTC |
| Cas12c (C2c3) | TA |
| Cas12d (CasY) | TA |
| Cas12e (CasX) | 5'-TTCN-3' |

In a preferred embodiment, the CRISPR effector protein may recognize a 3' PAM. In certain embodiments, the CRISPR effector protein may recognize a 3' PAM which is 5'H, wherein H is A, C or U.

Further, engineering of the PAM Interacting (PI) domain on the Cas protein may allow programing of PAM specificity, improve target site recognition fidelity, and increase the versatility of the CRISPR-Cas protein, for example as described for Cas9 in Kleinstiver B P et al. Engineered CRISPR-Cas9 nucleases with altered PAM specificities. Nature. 2015 Jul. 23; 523 (7561): 481-5. doi: 10.1038/nature14592. As further detailed herein, the skilled person will understand that Cas13 proteins may be modified analogously. Gao et al, "Engineered Cpf1 Enzymes with Altered PAM Specificities," bioRxiv 091611; doi: http://dx.doi.org/10.1101/091611 (Dec. 4, 2016). Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

PAM sequences can be identified in a polynucleotide using an appropriate design tool, which are commercially available as well as online. Such freely available tools include, but are not limited to, CRISPRFinder and CRISP-RTarget. Mojica et al. 2009. Microbiol. 155 (Pt. 3): 733-740; Atschul et al. 1990. J. Mol. Biol. 215:403-410; Biswass et al. 2013 RNA Biol. 10:817-827; and Grissa et al. 2007. Nucleic Acid Res. 35: W52-57. Experimental approaches to PAM identification can include, but are not limited to, plasmid depletion assays (Jiang et al. 2013. Nat. Biotechnol. 31:233-239; Esvelt et al. 2013. Nat. Methods. 10:1116-1121; Kleinstiver et al. 2015. Nature. 523:481-485), screened by a high-throughput in vivo model called PAM-SCNAR (Pattanayak et al. 2013. Nat. Biotechnol. 31:839-843 and Leenay et al. 2016. Mol. Cell. 16:253), and negative screening (Zetsche et al. 2015. Cell. 163:759-771).

As previously mentioned, CRISPR-Cas systems that target RNA do not typically rely on PAM sequences. Instead such systems typically recognize protospacer flanking sites (PFSs) instead of PAMs Thus, Type VI CRISPR-Cas systems typically recognize protospacer flanking sites (PFSs) instead of PAMs. PFSs represents an analogue to PAMs for RNA targets. Type VI CRISPR-Cas systems employ a Cas13. Some Cas13 proteins analyzed to date, such as Cas13a (C2c2) identified from Leptotrichia shahii (LShCAs13a) have a specific discrimination against G at the 3'end of the target RNA. The presence of a C at the corresponding crRNA repeat site can indicate that nucleotide pairing at this position is rejected. However, some Cas13 proteins (e.g., LwaCAs13a and PspCas13b) do not seem to have a PFS preference. See e.g., Gleditzsch et al. 2019. RNA Biology. 16 (4): 504-517.

Some Type VI proteins, such as subtype B, have 5'-recognition of D (G, T, A) and a 3'-motif requirement of NAN or NNA. One example is the Cas13b protein identified in Bergeyella zoohelcum (BzCas13b). See e.g., Gleditzsch et al. 2019. RNA Biology. 16 (4): 504-517.

Overall Type VI CRISPR-Cas systems appear to have less restrictive rules for substrate (e.g., target sequence) recognition than those that target DNA (e.g., Type V and type II).

Sequences Related to Nucleus Targeting and Transportation

In some embodiments, one or more components (e.g., the Cas protein and/or deaminase) in the composition for engineering cells may comprise one or more sequences related to nucleus targeting and transportation. Such sequence may facilitate the one or more components in the composition for targeting a sequence within a cell. In order to improve targeting of the CRISPR-Cas protein and/or the nucleotide deaminase protein or catalytic domain thereof used in the methods of the present disclosure to the nucleus, it may be advantageous to provide one or both of these components with one or more nuclear localization sequences (NLSs).

In some embodiments, the NLSs used in the context of the present disclosure are heterologous to the proteins. Non-limiting examples of NLSs include an NLS sequence derived from the NLS of the SV40 virus large T-antigen, having the amino acid sequence PKKKRKV (SEQ ID No. 1) or PKKKRKVEAS (SEQ ID No. 17); the NLS from nucleoplasmin (e.g., the nucleoplasmin bipartite NLS with the sequence KRPAATKKAGQAKKKK (SEQ ID No. 2)); the c-myc NLS having the amino acid sequence PAAKRVKLD (SEQ ID No. 3) or RQRRNELKRSP (SEQ ID No. 4); the hRNPA1 NLS having the sequence M9 NQSSNFGPM-KGGNFGGRSSGPYGGGGQYFAKPRNQGGY (SEQ ID No. 5); the sequence RMRIZFKNKGKDTAELRRRR-VEVSVELRKAKKDEQILKRRNV (SEQ ID No. 6) of the IBB domain from importin-alpha; the sequences VSRKR-PRP (SEQ ID No. 7) and PPKKARED (SEQ ID No. 8) of the myoma T protein; the sequence PQPKKKPL (SEQ ID No. 9) of human p53; the sequence SALIKKKKMAP (SEQ ID No. 10) of mouse c-abl IV; the sequences DRLRR (SEQ ID No. 11) and PKQKKRK (SEQ ID No. 12) of the influenza virus NS1; the sequence RKLKKKIKKL (SEQ ID No. 13) of the Hepatitis virus delta antigen; the sequence REKKKFLKRR (SEQ ID No. 14) of the mouse Mx1 protein; the sequence KRKGDEVDGVDEVAKKKSKK (SEQ ID No. 15) of the human poly(ADP-ribose) polymerase; and the sequence RKCLQAGMNLEARKTKK (SEQ ID No. 16) of the steroid hormone receptors (human) glucocorticoid. In general, the one or more NLSs are of sufficient strength to drive accumulation of the DNA-targeting Cas protein in a detectable amount in the nucleus of a eukaryotic cell. In general, strength of nuclear localization activity may derive from the number of NLSs in the CRISPR-Cas protein, the particular NLS(s) used, or a combination of these factors. Detection of accumulation in the nucleus may be performed by any suitable technique. For example, a detectable marker may be fused to the nucleic acid-targeting protein, such that location within a cell may be visualized, such as in combination with a means for detecting the location of the nucleus (e.g., a stain specific for the nucleus such as DAPI). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of nucleic acid-targeting complex formation (e.g., assay for deaminase activity) at the target sequence, or assay for altered gene expression activity affected by DNA-targeting complex formation and/or DNA-targeting), as compared to a control not exposed to the CRISPR-Cas protein and deaminase protein, or exposed to a CRISPR-Cas and/or deaminase protein lacking the one or more NLSs.

The CRISPR-Cas and/or nucleotide deaminase proteins may be provided with 1 or more, such as with, 2, 3, 4, 5, 6, 7, 8, 9, 10, or more heterologous NLSs. In some embodiments, the proteins comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g., zero or at least one or more NLS at the amino-terminus and zero or at one or more NLS at the carboxy terminus). When more than one NLS is present, each may be selected independently of the others, such that a single NLS may be present in more than one copy and/or in combination with one or more other NLSs present in one or more copies. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. In preferred embodiments of the CRISPR-Cas proteins, an NLS attached to the C-terminal of the protein.

In certain embodiments, guides of the disclosure comprise specific binding sites (e.g. aptamers) for adapter proteins, which may be linked to or fused to an nucleotide deaminase or catalytic domain thereof. When such a guide forms a CRISPR complex (e.g., CRISPR-Cas protein binding to guide and target) the adapter proteins bind and, the nucleotide deaminase or catalytic domain thereof associated with the adapter protein is positioned in a spatial orientation which is advantageous for the attributed function to be effective.

The skilled person will understand that modifications to the guide which allow for binding of the adapter+nucleotide deaminase, but not proper positioning of the adapter+ nucleotide deaminase (e.g., due to steric hindrance within the three dimensional structure of the CRISPR complex) are modifications which are not intended. The one or more modified guide may be modified at the tetra loop, the stem loop 1, stem loop 2, or stem loop 3, as described herein, preferably at either the tetra loop or stem loop 2, and in some cases at both the tetra loop and stem loop 2.

In some embodiments, a component (e.g., the dead Cas protein, the nucleotide deaminase protein or catalytic domain thereof, or a combination thereof) in the systems may comprise one or more nuclear export signals (NES), one or more nuclear localization signals (NLS), or any combinations thereof. In some cases, the NES may be an HIV Rev NES. In certain cases, the NES may be MAPK NES. When the component is a protein, the NES or NLS may be at the C terminus of component. Alternatively or additionally, the NES or NLS may be at the N terminus of component. In some examples, the Cas protein and optionally said nucleotide deaminase protein or catalytic domain thereof comprise one or more heterologous nuclear export signal(s) (NES(s)) or nuclear localization signal(s) (NLS(s)), preferably an HIV Rev NES or MAPK NES, preferably C-terminal.

Templates

In some embodiments, the composition for engineering cells comprise a template, e.g., a recombination template. A template may be a component of another vector as described herein, contained in a separate vector, or provided as a separate polynucleotide. In some embodiments, a recombination template is designed to serve as a template in homologous recombination, such as within or near a target sequence nicked or cleaved by a nucleic acid-targeting effector protein as a part of a nucleic acid-targeting complex.

In an embodiment, the template nucleic acid alters the sequence of the target position. In an embodiment, the template nucleic acid results in the incorporation of a modified, or non-naturally occurring base into the target nucleic acid.

The template sequence may undergo a breakage mediated or catalyzed recombination with the target sequence. In an embodiment, the template nucleic acid may include a sequence that corresponds to a site on the target sequence that is cleaved by a Cas protein mediated cleavage event. In an embodiment, the template nucleic acid may include a sequence that corresponds to both, a first site on the target sequence that is cleaved in a first Cas protein mediated event, and a second site on the target sequence that is cleaved in a second Cas protein mediated event.

In certain embodiments, the template nucleic acid can include a sequence which results in an alteration in the coding sequence of a translated sequence, e.g., one which results in the substitution of one amino acid for another in a protein product, e.g., transforming a mutant allele into a wild type allele, transforming a wild type allele into a mutant allele, and/or introducing a stop codon, insertion of an amino acid residue, deletion of an amino acid residue, or a nonsense mutation. In certain embodiments, the template nucleic acid can include sequence which results in an alteration in a non-coding sequence, e.g., an alteration in an exon or in a 5' or 3' non-translated or non-transcribed region. Such alterations include an alteration in a control element, e.g., a promoter, enhancer, and an alteration in a cis-acting or trans-acting control element.

A template nucleic acid having homology with a target position in a target gene may be used to alter the structure of a target sequence. The template sequence may be used to alter an unwanted structure, e.g., an unwanted or mutant nucleotide. The template nucleic acid may include a sequence which, when integrated, results in decreasing the activity of a positive control element; increasing the activity of a positive control element; decreasing the activity of a negative control element; increasing the activity of a negative control element; decreasing the expression of a gene; increasing the expression of a gene; increasing resistance to a disorder or disease; increasing resistance to viral entry; correcting a mutation or altering an unwanted amino acid residue conferring, increasing, abolishing or decreasing a biological property of a gene product, e.g., increasing the enzymatic activity of an enzyme, or increasing the ability of a gene product to interact with another molecule.

The template nucleic acid may include a sequence which results in a change in sequence of 1, 2, 3, 4, 5, 6, 7, 8, 9, 10, 11, 12 or more nucleotides of the target sequence.

A template polynucleotide may be of any suitable length, such as about or more than about 10, 15, 20, 25, 50, 75, 100, 150, 200, 500, 1000, or more nucleotides in length. In an embodiment, the template nucleic acid may be 20+/−10, 30+/−10, 40+/−10, 50+/−10, 60+/−10, 70+/−10, 80+/−10, 90+/−10, 100+/−10, 110+/−10, 120+/−10, 130+/−10, 140+/−10, 150+/−10, 160+/−10, 170+/−10, 180+/−10, 190+/−10, 200+/−10, 210+/−10, of 220+/−10 nucleotides in length. In an embodiment, the template nucleic acid may be 30+/−20, 40+/−20, 50+/−20, 60+/−20, 70+/−20, 80+/−20, 90+/−20, 100+/−20, 110+/−20, 120+/−20, 130+/−20, 140+/−20, I 50+/−20, 160+/−20, 170+/−20, 180+/−20, 190+/−20, 200+/−20, 210+/−20, of 220+/−20 nucleotides in length. In an embodiment, the template nucleic acid is 10 to 1,000, 20 to 900, 30 to 800, 40 to 700, 50 to 600, 50 to 500, 50 to 400, 50 to 300, 50 to 200, or 50 to 100 nucleotides in length.

In some embodiments, the template polynucleotide is complementary to a portion of a polynucleotide comprising the target sequence. When optimally aligned, a template polynucleotide might overlap with one or more nucleotides of a target sequences (e.g., about or more than about 1, 5, 10, 15, 20, 25, 30, 35, 40, 45, 50, 60, 70, 80, 90, 100 or more nucleotides). In some embodiments, when a template sequence and a polynucleotide comprising a target sequence are optimally aligned, the nearest nucleotide of the template polynucleotide is within about 1, 5, 10, 15, 20, 25, 50, 75, 100, 200, 300, 400, 500, 1000, 5000, 10000, or more nucleotides from the target sequence.

The exogenous polynucleotide template comprises a sequence to be integrated (e.g., a mutated gene). The sequence for integration may be a sequence endogenous or exogenous to the cell. Examples of a sequence to be integrated include polynucleotides encoding a protein or a non-coding RNA (e.g., a microRNA). Thus, the sequence for integration may be operably linked to an appropriate control sequence or sequences. Alternatively, the sequence to be integrated may provide a regulatory function.

An upstream or downstream sequence may comprise from about 20 bp to about 2500 bp, for example, about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 bp. In some methods, the exemplary upstream or downstream sequence have about 200 bp to about 2000 bp, about 600 bp to about 1000 bp, or more particularly about 700 bp to about 1000.

An upstream or downstream sequence may comprise from about 20 bp to about 2500 bp, for example, about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 bp. In some methods, the exemplary upstream or downstream sequence have about 200 bp to about 2000 bp, about 600 bp to about 1000 bp, or more particularly about 700 bp to about 1000.

In certain embodiments, one or both homology arms may be shortened to avoid including certain sequence repeat elements. For example, a 5' homology arm may be shortened to avoid a sequence repeat element. In other embodiments, a 3' homology arm may be shortened to avoid a sequence repeat element. In some embodiments, both the 5' and the 3' homology arms may be shortened to avoid including certain sequence repeat elements.

In some methods, the exogenous polynucleotide template may further comprise a marker. Such a marker may make it easy to screen for targeted integrations. Examples of suitable markers include restriction sites, fluorescent proteins, or selectable markers. The exogenous polynucleotide template of the disclosure can be constructed using recombinant techniques (see, for example, Sambrook et al., 2001 and Ausubel et al., 1996).

In certain embodiments, a template nucleic acid for correcting a mutation may designed for use as a single-stranded oligonucleotide. When using a single-stranded oligonucleotide, 5' and 3' homology arms may range up to about 200 base pairs (bp) in length, e.g., at least 25, 50, 75, 100, 125, 150, 175, or 200 bp in length.

Suzuki et al. describe in vivo genome editing via CRISPR/Cas9 mediated homology-independent targeted integration (2016, Nature 540:144-149).

Delivery

The present disclosure also provides delivery systems for introducing components of the systems and compositions herein to cells, tissues, organs, or organisms. A delivery system may comprise one or more delivery vehicles and/or cargos. Exemplary delivery systems and methods include those described in paragraphs to of Feng Zhang et al., (International Patent Publication No. WO 2016/106236A1), and pages 1241-1251 and Table 1 of Lino C A et al., Delivering CRISPR: a review of the challenges and approaches, DRUG DELIVERY, 2018, VOL. 25, NO. 1, 1234-1257, which are incorporated by reference herein in their entireties.

Cargos

The delivery systems may comprise one or more cargos. The cargos may comprise one or more components of the systems and compositions herein. A cargo may comprise one or more of the following: i) a plasmid encoding one or more Cas proteins; ii) a plasmid encoding one or more guide RNAs; iii) mRNA of one or more Cas proteins; iv) one or more guide RNAs; v) one or more Cas proteins; vi) any combination thereof. In some examples, a cargo may comprise a plasmid encoding one or more Cas protein and one or more (e.g., a plurality of) guide RNAs. In some embodiments, a cargo may comprise mRNA encoding one or more Cas proteins and one or more guide RNAs.

In some examples, a cargo may comprise one or more Cas proteins and one or more guide RNAs, e.g., in the form of ribonucleoprotein complexes (RNP). The ribonucleoprotein complexes may be delivered by methods and systems herein. In some cases, the ribonucleoprotein may be delivered by way of a polypeptide-based shuttle agent. In one example, the ribonucleoprotein may be delivered using synthetic peptides comprising an endosome leakage domain (ELD) operably linked to a cell penetrating domain (CPD), to a histidine-rich domain and a CPD, e.g., as describe in International Patent Publication No. WO 2016/161516.

Physical Delivery

In some embodiments, the cargos may be introduced to cells by physical delivery methods. Examples of physical methods include microinjection, electroporation, and hydrodynamic delivery.

Microinjection

Microinjection of the cargo directly to cells can achieve high efficiency, e.g., above 90% or about 100%. In some embodiments, microinjection may be performed using a microscope and a needle (e.g., with 0.5-5.0 µm in diameter) to pierce a cell membrane and deliver the cargo directly to a target site within the cell. Microinjection may be used for in vitro and ex vivo delivery.

Plasmids comprising coding sequences for Cas proteins and/or guide RNAs, mRNAs, and/or guide RNAs, may be microinjected. In some cases, microinjection may be used i) to deliver DNA directly to a cell nucleus, and/or ii) to deliver mRNA (e.g., in vitro transcribed) to a cell nucleus or cytoplasm. In certain examples, microinjection may be used to delivery sgRNA directly to the nucleus and Cas-encoding mRNA to the cytoplasm, e.g., facilitating translation and shuttling of Cas to the nucleus.

Microinjection may be used to generate genetically modified animals. For example, gene editing cargos may be injected into zygotes to allow for efficient germline modification. Such approach can yield normal embryos and full-term mouse pups harboring the desired modification(s). Microinjection can also be used to provide transiently up- or down-regulate a specific gene within the genome of a cell, e.g., using CRISPRa and CRISPRi.

Electroporation

In some embodiments, the cargos and/or delivery vehicles may be delivered by electroporation. Electroporation may use pulsed high-voltage electrical currents to transiently open nanometer-sized pores within the cellular membrane of cells suspended in buffer, allowing for components with hydrodynamic diameters of tens of nanometers to flow into the cell. In some cases, electroporation may be used on various cell types and efficiently transfer cargo into cells. Electroporation may be used for in vitro and ex vivo delivery.

Electroporation may also be used to deliver the cargo to into the nuclei of mammalian cells by applying specific voltage and reagents, e.g., by nucleofection. Such approaches include those described in Wu Y, et al. (2015). Cell Res 25:67-79; Ye L, et al. (2014). Proc Natl Acad Sci USA 111:9591-6; Choi P S, Meyerson M. (2014). Nat Commun 5:3728; Wang J, Quake S R. (2014). Proc Natl Acad Sci 111:13157-62. Electroporation may also be used to deliver the cargo in vivo, e.g., with methods described in Zuckermann M, et al. (2015). Nat Commun 6:7391.

Hydrodynamic Delivery

Hydrodynamic delivery may also be used for delivering the cargos, e.g., for in vivo delivery. In some examples, hydrodynamic delivery may be performed by rapidly pushing a large volume (8-10% body weight) solution containing the gene editing cargo into the bloodstream of a subject (e.g., an animal or human), e.g., for mice, via the tail vein. As blood is incompressible, the large bolus of liquid may result in an increase in hydrodynamic pressure that temporarily enhances permeability into endothelial and parenchymal cells, allowing for cargo not normally capable of crossing a cellular membrane to pass into cells. This approach may be used for delivering naked DNA plasmids and proteins. The delivered cargos may be enriched in liver, kidney, lung, muscle, and/or heart.

Transfection

The cargos, e.g., nucleic acids, may be introduced to cells by transfection methods for introducing nucleic acids into cells. Examples of transfection methods include calcium phosphate-mediated transfection, cationic transfection, liposome transfection, dendrimer transfection, heat shock transfection, magnetofection, lipofection, impalefection, optical transfection, and proprietary agent-enhanced uptake of nucleic acid.

Delivery Vehicles

The delivery systems may comprise one or more delivery vehicles. The delivery vehicles may deliver the cargo into cells, tissues, organs, or organisms (e.g., animals or plants). The cargos may be packaged, carried, or otherwise associated with the delivery vehicles. The delivery vehicles may be selected based on the types of cargo to be delivered, and/or the delivery is in vitro and/or in vivo. Examples of delivery vehicles include vectors, viruses, non-viral vehicles, and other delivery reagents described herein.

The delivery vehicles in accordance with the present invention may have a greatest dimension (e.g., diameter) of less than 100 microns (µm). In some embodiments, the delivery vehicles have a greatest dimension of less than 10 µm. In some embodiments, the delivery vehicles may have a greatest dimension of less than 2000 nanometers (nm). In some embodiments, the delivery vehicles may have a greatest dimension of less than 1000 nanometers (nm). In some embodiments, the delivery vehicles may have a greatest dimension (e.g., diameter) of less than 900 nm, less than 800 nm, less than 700 nm, less than 600 nm, less than 500 nm, less than 400 nm, less than 300 nm, less than 200 nm, less than 150 nm, or less than 100 nm, less than 50 nm. In some embodiments, the delivery vehicles may have a greatest dimension ranging between 25 nm and 200 nm.

In some embodiments, the delivery vehicles may be or comprise particles. For example, the delivery vehicle may be or comprise nanoparticles (e.g., particles with a greatest dimension (e.g., diameter) no greater than 1000 nm. The particles may be provided in different forms, e.g., as solid particles (e.g., metal such as silver, gold, iron, titanium), non-metal, lipid-based solids, polymers), suspensions of particles, or combinations thereof. Metal, dielectric, and semiconductor particles may be prepared, as well as hybrid structures (e.g., core-shell particles).

Vectors

The systems, compositions, and/or delivery systems may comprise one or more vectors. The present disclosure also include vector systems. A vector system may comprise one or more vectors. In some embodiments, a vector refers to a nucleic acid molecule capable of transporting another nucleic acid to which it has been linked. Vectors include nucleic acid molecules that are single-stranded, double-stranded, or partially double-stranded; nucleic acid molecules that comprise one or more free ends, no free ends (e.g., circular); nucleic acid molecules that comprise DNA, RNA, or both; and other varieties of polynucleotides known in the art. A vector may be a plasmid, e.g., a circular double stranded DNA loop into which additional DNA segments can be inserted, such as by standard molecular cloning techniques. Certain vectors may be capable of autonomous replication in a host cell into which they are introduced (e.g., bacterial vectors having a bacterial origin of replication and episomal mammalian vectors). Some vectors (e.g., non-episomal mammalian vectors) are integrated into the genome of a host cell upon introduction into the host cell, and thereby are replicated along with the host genome. In certain examples, vectors may be expression vectors, e.g., capable of directing the expression of genes to which they are operatively-linked. In some cases, the expression vectors may be for expression in eukaryotic cells. Common expression vectors of utility in recombinant DNA techniques are often in the form of plasmids.

Examples of vectors include pGEX, pMAL, pRIT5, *E. coli* expression vectors (e.g., pTrc, pET 11d, yeast expression vectors (e.g., pYepSec1, pMFa, pJRY88, pYES2, and picZ, Baculovirus vectors (e.g., for expression in insect cells such as SF9 cells) (e.g., pAc series and the pVL series), mammalian expression vectors (e.g., pCDM8 and pMT2PC.

A vector may comprise i) Cas encoding sequence(s), and/or ii) a single, or at least 2, at least 3, at least 4, at least 5, at least 6, at least 7, at least 8, at least 9, at least 10, at least 12, at least 14, at least 16, at least 32, at least 48, at least 50 guide RNA(s) encoding sequences. In a single vector there can be a promoter for each RNA coding sequence. Alternatively or additionally, in a single vector, there may be a promoter controlling (e.g., driving transcription and/or expression) multiple RNA encoding sequences.

Regulatory Elements

A vector may comprise one or more regulatory elements. The regulatory element(s) may be operably linked to coding sequences of Cas proteins, accessary proteins, guide RNAs (e.g., a single guide RNA, crRNA, and/or tracrRNA), or combination thereof. The term "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). In certain examples, a vector may comprise a first regulatory element operably linked to a nucleotide sequence encoding a Cas protein, and a second regulatory element operably linked to a nucleotide sequence encoding a guide RNA.

Examples of regulatory elements include promoters, enhancers, internal ribosomal entry sites (IRES), and other expression control elements (e.g., transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g., liver, pancreas), or particular cell types (e.g., lymphocytes). Regulatory elements may also direct expression in a temporal-dependent manner, such as in a cell-cycle dependent or developmental stage-dependent manner, which may or may not also be tissue or cell-type specific.

Examples of promoters include one or more pol III promoters (e.g., 1, 2, 3, 4, 5, or more pol III promoters), one or more pol II promoters (e.g., 1, 2, 3, 4, 5, or more pol II promoters), one or more pol I promoters (e.g., 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer), the SV40 promoter, the dihydrofolate reductase promoter, the β-actin promoter, the phosphoglycerol kinase (PGK) promoter, and the EF1α promoter.

Viral Vectors

The cargos may be delivered by viruses. In some embodiments, viral vectors are used. A viral vector may comprise virally-derived DNA or RNA sequences for packaging into a virus (e.g., retroviruses, replication defective retroviruses, adenoviruses, replication defective adenoviruses, and adeno-associated viruses). Viral vectors also include polynucleotides carried by a virus for transfection into a host cell. Viruses and viral vectors may be used for in vitro, ex vivo, and/or in vivo deliveries.

In some embodiments, the viral vectors may have a tropism allowing neural delivery. Examples of the vectors include herpes simplex virus type 1 vectors, pseudotyped lentiviral vectors, adenoviral vectors, AAV vectors with neural tropism. Vectors with neurotropism include those described in Steven J Gray et al., Viral vectors and delivery strategies for CNS gene therapy, Ther Deliv. 2010 October; 1 (4): 517-534.

Adeno Associated Virus (AAV)

The systems and compositions herein may be delivered by adeno associated virus (AAV). AAV vectors may be used for such delivery. AAV, of the Dependovirus genus and Parvoviridae family, is a single stranded DNA virus. In some embodiments, AAV may provide a persistent source of the provided DNA, as AAV delivered genomic material can exist indefinitely in cells, e.g., either as exogenous DNA or, with some modification, may be directly integrated into the host DNA. In some embodiments, AAV do not cause or relate with any diseases in humans. The virus itself is able to efficiently infect cells while provoking little to no innate or adaptive immune response or associated toxicity.

Examples of AAV that can be used herein include AAV-1, AAV-2, AAV-3, AAV-4, AAV-5, AAV-6, AAV-8, and AAV-9. The type of AAV may be selected with regard to the cells to be targeted; e.g., one can select AAV serotypes 1, 2, 5 or a hybrid capsid AAV1, AAV2, AAV5 or any combination thereof for targeting brain or neuronal cells; and one can select AAV4 for targeting cardiac tissue. AAV8 is useful for delivery to the liver. AAV-2-based vectors were originally proposed for CFTR delivery to CF airways, other serotypes such as AAV-1, AAV-5, AAV-6, and AAV-9 exhibit improved gene transfer efficiency in a variety of models of the lung epithelium. Examples of cell types targeted by AAV are described in Grimm, D. et al, J. Virol. 82:5887-5911 (2008)), and shown as follows:

| | Cell Line | | | | | | | |
|---|---|---|---|---|---|---|---|---|
| | AAV-1 | AAV-2 | AAV-3 | AAV-4 | AAV-5 | AAV-6 | AAV-8 | AAV-9 |
| Huh-7 | 13 | 100 | 2.5 | 0.0 | 0.1 | 10 | 0.7 | 0.0 |
| HEK293 | 25 | 100 | 2.5 | 0.1 | 0.1 | 5 | 0.7 | 0.1 |
| HeLa | 3 | 100 | 2.0 | 0.1 | 6.7 | 1 | 0.2 | 0.1 |
| HepG2 | 3 | 100 | 16.7 | 0.3 | 1.7 | 5 | 0.3 | ND |
| Hep1A | 20 | 100 | 0.2 | 1.0 | 0.1 | 1 | 0.2 | 0.0 |
| 911 | 17 | 100 | 11 | 0.2 | 0.1 | 17 | 0.1 | ND |
| CHO | 100 | 100 | 14 | 1.4 | 333 | 50 | 10 | 1.0 |
| COS | 33 | 100 | 33 | 3.3 | 5.0 | 14 | 2.0 | 0.5 |
| MeWo | 10 | 100 | 20 | 0.3 | 6.7 | 10 | 1.0 | 0.2 |
| NIH3T3 | 10 | 100 | 2.9 | 2.9 | 0.3 | 10 | 0.3 | ND |
| A549 | 14 | 100 | 20 | ND | 0.5 | 10 | 0.5 | 0.1 |
| HT1180 | 20 | 100 | 10 | 0.1 | 0.3 | 33 | 0.5 | 0.1 |
| Monocytes | 1111 | 100 | ND | ND | 125 | 1429 | ND | ND |
| Immature DC | 2500 | 100 | ND | ND | 222 | 2857 | ND | ND |
| Mature DC | 2222 | 100 | ND | ND | 333 | 3333 | ND | ND |

CRISPR-Cas AAV particles may be created in HEK 293 T cells. Once particles with specific tropism have been created, they are used to infect the target cell line much in the same way that native viral particles do. This may allow for persistent presence of CRISPR-Cas components in the infected cell type, and what makes this version of delivery particularly suited to cases where long-term expression is desirable. Examples of doses and formulations for AAV that can be used include those describe in U.S. Pat. Nos. 8,454,972 and 8,404,658.

Various strategies may be used for delivery the systems and compositions herein with AAVs. In some examples, coding sequences of Cas and gRNA may be packaged directly onto one DNA plasmid vector and delivered via one AAV particle. In some examples, AAVs may be used to deliver gRNAs into cells that have been previously engineered to express Cas. In some examples, coding sequences of Cas and gRNA may be made into two separate AAV particles, which are used for co-transfection of target cells. In some examples, markers, tags, and other sequences may be packaged in the same AAV particles as coding sequences of Cas and/or gRNAs.

Lentiviruses

The systems and compositions herein may be delivered by lentiviruses. Lentiviral vectors may be used for such delivery. Lentiviruses are complex retroviruses that have the ability to infect and express their genes in both mitotic and post-mitotic cells.

Examples of lentiviruses include human immunodeficiency virus (HIV), which may use its envelope glycoproteins of other viruses to target a broad range of cell types; minimal non-primate lentiviral vectors based on the equine infectious anemia virus (EIAV), which may be used for ocular therapies. In certain embodiments, self-inactivating lentiviral vectors with an siRNA targeting a common exon shared by HIV tat/rev, a nucleolar-localizing TAR decoy, and an anti-CCR5-specific hammerhead ribozyme (see, e.g., DiGiusto et al. (2010) Sci Transl Med 2: 36ra43) may be used and/or adapted to the nucleic acid-targeting system herein.

Lentiviruses may be pseudo-typed with other viral proteins, such as the G protein of vesicular stomatitis virus. In doing so, the cellular tropism of the lentiviruses can be altered to be as broad or narrow as desired. In some cases, to improve safety, second- and third-generation lentiviral systems may split essential genes across three plasmids, which may reduce the likelihood of accidental reconstitution of viable viral particles within cells.

In some examples, leveraging the integration ability, lentiviruses may be used to create libraries of cells comprising various genetic modifications, e.g., for screening and/or studying genes and signaling pathways.

Adenoviruses

The systems and compositions herein may be delivered by adenoviruses. Adenoviral vectors may be used for such delivery. Adenoviruses include nonenveloped viruses with an icosahedral nucleocapsid containing a double stranded DNA genome. Adenoviruses may infect dividing and non-dividing cells. In some embodiments, adenoviruses do not integrate into the genome of host cells, which may be used for limiting off-target effects of CRISPR-Cas systems in gene editing applications.

Non-Viral Vehicles

The delivery vehicles may comprise non-viral vehicles. In general, methods and vehicles capable of delivering nucleic acids and/or proteins may be used for delivering the systems compositions herein. Examples of non-viral vehicles include lipid nanoparticles, cell-penetrating peptides (CPPs), DNA nanoclews, gold nanoparticles, streptolysin O, multifunctional envelope-type nanodevices (MENDs), lipid-coated mesoporous silica particles, and other inorganic nanoparticles.

Lipid Particles

The delivery vehicles may comprise lipid particles, e.g., lipid nanoparticles (LNPs) and liposomes.

Lipid Nanoparticles (LNPs)

LNPs may encapsulate nucleic acids within cationic lipid particles (e.g., liposomes), and may be delivered to cells with relative ease. In some examples, lipid nanoparticles do not contain any viral components, which helps minimize safety and immunogenicity concerns. Lipid particles may be used for in vitro, ex vivo, and in vivo deliveries. Lipid particles may be used for various scales of cell populations.

In some examples. LNPs may be used for delivering DNA molecules (e.g., those comprising coding sequences of Cas and/or gRNA) and/or RNA molecules (e.g., mRNA of Cas, gRNAs). In certain cases, LNPs may be use for delivering RNP complexes of Cas/gRNA.

Components in LNPs may comprise cationic lipids 1,2-dilinoleoyl-3-dimethylammonium-propane (DLinDAP), 1,2-dilinoleyloxy-3-N,N-dimethylaminopropane (DLinDMA), 1,2-dilinoleyloxyketo-N,N-dimethyl-3-aminopropane (DLinK-DMA), 1,2-dilinoleyl-4-(2-dimethylaminoethyl)-[1,3]-dioxolane (DLinKC2-DMA), (3-o-[2"-(methoxypolyethyleneglycol 2000) succinoyl]-1,2-dimyristoyl-sn-glycol (PEG-S-DMG), R-3-[(w-methoxy-poly(ethylene glycol) 2000) carbamoyl]-1,2-dimyristyloxlpropyl-3-amine (PEG-C-DOMG, and any combination thereof. Preparation of LNPs and encapsulation may be adapted from Rosin et al, Molecular Therapy, vol. 19, no. 12, pages 1286-220 December 2011).

Liposomes

In some embodiments, a lipid particle may be liposome. Liposomes are spherical vesicle structures composed of a uni- or multilamellar lipid bilayer surrounding internal aqueous compartments and a relatively impermeable outer lipophilic phospholipid bilayer. In some embodiments, liposomes are biocompatible, nontoxic, can deliver both hydrophilic and lipophilic drug molecules, protect their cargo from degradation by plasma enzymes, and transport their load across biological membranes and the blood brain barrier (BBB).

Liposomes can be made from several different types of lipids, e.g., phospholipids. A liposome may comprise natural phospholipids and lipids such as 1,2-distearoyl-sn-glycero-3-phosphatidyl choline (DSPC), sphingomyelin, egg phosphatidylcholines, monosialoganglioside, or any combination thereof.

Several other additives may be added to liposomes in order to modify their structure and properties. For instance, liposomes may further comprise cholesterol, sphingomyelin, and/or 1,2-dioleoyl-sn-glycero-3-phosphoethanolamine (DOPE), e.g., to increase stability and/or to prevent the leakage of the liposomal inner cargo.

Stable Nucleic-Acid-Lipid Particles (SNALPs)

In some embodiments, the lipid particles may be stable nucleic acid lipid particles (SNALPs). SNALPs may comprise an ionizable lipid (DLinDMA) (e.g., cationic at low pH), a neutral helper lipid, cholesterol, a diffusible polyethylene glycol (PEG)-lipid, or any combination thereof. In some examples, SNALPs may comprise synthetic cholesterol, dipalmitoylphosphatidylcholine, 3-N-[(w-methoxy polyethylene glycol) 2000) carbamoyl]-1,2-dimyristyloxypropylamine, and cationic 1,2-dilinoleyloxy-3-(N;N-dimethyl)aminopropane. In some examples, SNALPs may comprise synthetic cholesterol, 1,2-distearoyl-sn-glycero-3-phosphocholine, PEG-CDMA, and 1,2-dilinoleyloxy-3-(N; N-dimethyl)aminopropane (DLinDMA).

Other Lipids

The lipid particles may also comprise one or more other types of lipids, e.g., cationic lipids, such as amino lipid 2,2-dilinoleyl-4-dimethylaminoethyl-[1,3]-dioxolane (DLin-KC2-DMA), DLin-KC2-DMA4, C12-200 and co-lipids distearoylphosphatidyl choline, cholesterol, and PEG-DMG.

Lipoplexes/Polyplexes

In some embodiments, the delivery vehicles comprise lipoplexes and/or polyplexes. Lipoplexes may bind to negatively charged cell membrane and induce endocytosis into the cells. Examples of lipoplexes may be complexes comprising lipid(s) and non-lipid components. Examples of lipoplexes and polyplexes include FuGENE-6 reagent, a non-liposomal solution containing lipids and other components, zwitterionic amino lipids (ZALs), Ca2þ (e.g., forming DNA/$Ca^{2+}$ microcomplexes), polyethylenimine (PEI) (e.g., branched PEI), and poly(L-lysine) (PLL).

Cell Penetrating Peptides

In some embodiments, the delivery vehicles comprise cell penetrating peptides (CPPs). CPPs are short peptides that facilitate cellular uptake of various molecular cargo (e.g., from nanosized particles to small chemical molecules and large fragments of DNA).

CPPs may be of different sizes, amino acid sequences, and charges. In some examples, CPPs can translocate the plasma membrane and facilitate the delivery of various molecular cargoes to the cytoplasm or an organelle. CPPs may be introduced into cells via different mechanisms, e.g., direct penetration in the membrane, endocytosis-mediated entry, and translocation through the formation of a transitory structure.

CPPs may have an amino acid composition that either contains a high relative abundance of positively charged amino acids such as lysine or arginine or has sequences that contain an alternating pattern of polar/charged amino acids and non-polar, hydrophobic amino acids. These two types of structures are referred to as polycationic or amphipathic, respectively. A third class of CPPs are the hydrophobic peptides, containing only apolar residues, with low net charge or have hydrophobic amino acid groups that are crucial for cellular uptake. Another type of CPPs is the trans-activating transcriptional activator (Tat) from Human Immunodeficiency Virus 1 (HIV-1). Examples of CPPs include to Penetratin, Tat (48-60), Transportan, and (R-AhX-R4) (Ahx refers to aminohexanoyl). Examples of CPPs and related applications also include those described in U.S. Pat. No. 8,372,951.

CPPs can be used for in vitro and ex vivo work quite readily, and extensive optimization for each cargo and cell type is usually required. In some examples, CPPs may be covalently attached to the Cas protein directly, which is then complexed with the gRNA and delivered to cells. In some examples, separate delivery of CPP-Cas and CPP-gRNA to multiple cells may be performed. CPP may also be used to delivery RNPs.

DNA Nanoclews

In some embodiments, the delivery vehicles comprise DNA nanoclews. A DNA nanoclew refers to a sphere-like structure of DNA (e.g., with a shape of a ball of yarn). The nanoclew may be synthesized by rolling circle amplification with palindromic sequences that aide in the self-assembly of the structure. The sphere may then be loaded with a payload. An example of DNA nanoclew is described in Sun W et al, J Am Chem Soc. 2014 Oct. 22; 136 (42): 14722-5; and Sun W et al, Angew Chem Int Ed Engl. 2015 Oct. 5; 54 (41): 12029-33. DNA nanoclew may have a palindromic sequences to be partially complementary to the gRNA within the Cas: gRNA ribonucleoprotein complex. A DNA nanoclew may be coated, e.g., coated with PEI to induce endosomal escape.

Gold Nanoparticles

In some embodiments, the delivery vehicles comprise gold nanoparticles (also referred to AuNPs or colloidal gold). Gold nanoparticles may form complex with cargos, e.g., Cas: gRNA RNP. Gold nanoparticles may be coated, e.g., coated in a silicate and an endosomal disruptive polymer, PAsp (DET). Examples of gold nanoparticles include AuraSense Therapeutics' Spherical Nucleic Acid (SNATM) constructs, and those described in Mout R, et al. (2017). ACS Nano 11:2452-8; Lee K, et al. (2017). Nat Biomed Eng 1:889-901.

iTOP

In some embodiments, the delivery vehicles comprise iTOP. iTOP refers to a combination of small molecules which drives the highly efficient intracellular delivery of native proteins, independent of any transduction peptide. iTOP may be used for induced transduction by osmocytosis and propanebetaine, using NaCl-mediated hyperosmolality together with a transduction compound (propanebetaine) to trigger macropinocytotic uptake into cells of extracellular macromolecules. Examples of iTOP methods and reagents include those described in D'Astolfo D S, Pagliero R J, Pras A, et al. (2015). Cell 161:674-690.

Polymer-Based Particles

In some embodiments, the delivery vehicles may comprise polymer-based particles (e.g., nanoparticles). In some embodiments, the polymer-based particles may mimic a viral mechanism of membrane fusion. The polymer-based particles may be a synthetic copy of Influenza virus machinery and form transfection complexes with various types of nucleic acids ((siRNA, miRNA, plasmid DNA or shRNA, mRNA) that cells take up via the endocytosis pathway, a process that involves the formation of an acidic compartment. The low pH in late endosomes acts as a chemical switch that renders the particle surface hydrophobic and facilitates membrane crossing. Once in the cytosol, the particle releases its payload for cellular action. This Active Endosome Escape technology is safe and maximizes transfection efficiency as it is using a natural uptake pathway. In some embodiments, the polymer-based particles may comprise alkylated and carboxyalkylated branched polyethylenimine. In some examples, the polymer-based particles are VIROMER, e.g., VIROMER RNAi, VIROMER RED, VIROMER mRNA, VIROMER CRISPR. Example methods of delivering the systems and compositions herein include those described in Bawage S S et al., Synthetic mRNA expressed Cas13a mitigates RNA virus infections, www.biorxiv.org/content/10.1101/370460v1.full doi: doi.org/10.1101/370460, Viromer® RED, a powerful tool for transfection of keratinocytes. doi: 10.13140/ RG.2.2.16993.61281, Viromer® Transfection-Factbook 2018: technology, product overview, users' data., doi: 10.13140/RG.2.2.23912.16642.

Streptolysin O (SLO)

The delivery vehicles may be streptolysin O (SLO). SLO is a toxin produced by Group A streptococci that works by creating pores in mammalian cell membranes. SLO may act in a reversible manner, which allows for the delivery of proteins (e.g., up to 100 kDa) to the cytosol of cells without compromising overall viability. Examples of SLO include those described in Sierig G, et al. (2003). Infect Immun 71:446-55; Walev I, et al. (2001). Proc Natl Acad Sci USA 98:3185-90; Teng K W, et al. (2017). Elife 6: e25460.

Multifunctional Envelope-Type Nanodevice (MEND)

The delivery vehicles may comprise multifunctional envelope-type nanodevice (MENDs). MENDs may comprise condensed plasmid DNA, a PLL core, and a lipid film shell. A MEND may further comprise cell-penetrating peptide (e.g., stearyl octaarginine). The cell penetrating peptide may be in the lipid shell. The lipid envelope may be modified with one or more functional components, e.g., one or more of: polyethylene glycol (e.g., to increase vascular circulation time), ligands for targeting of specific tissues/ cells, additional cell-penetrating peptides (e.g., for greater cellular delivery), lipids to enhance endosomal escape, and nuclear delivery tags. In some examples, the MEND may be a tetra-lamellar MEND (T-MEND), which may target the cellular nucleus and mitochondria. In certain examples, a MEND may be a PEG-peptide-DOPE-conjugated MEND (PPD-MEND), which may target bladder cancer cells. Examples of MENDs include those described in Kogure K, et al. (2004). J Control Release 98:317-23; Nakamura T, et al. (2012). Acc Chem Res 45:1113-21.

Lipid-coated mesoporous silica particles

The delivery vehicles may comprise lipid-coated mesoporous silica particles. Lipid-coated mesoporous silica particles may comprise a mesoporous silica nanoparticle core and a lipid membrane shell. The silica core may have a large internal surface area, leading to high cargo loading capacities. In some embodiments, pore sizes, pore chemistry, and overall particle sizes may be modified for loading different types of cargos. The lipid coating of the particle may also be modified to maximize cargo loading, increase circulation times, and provide precise targeting and cargo release. Examples of lipid-coated mesoporous silica particles include those described in Du X, et al. (2014). Biomaterials 35:5580-90; Durfee P N, et al. (2016). ACS Nano 10:8325-45.

Inorganic Nanoparticles

The delivery vehicles may comprise inorganic nanoparticles. Examples of inorganic nanoparticles include carbon nanotubes (CNTs) (e.g., as described in Bates K and Kostarelos K. (2013). Adv Drug Deliv Rev 65:2023-33.), bare mesoporous silica nanoparticles (MSNPs) (e.g., as described in Luo G F, et al. (2014). Sci Rep 4:6064), and dense silica nanoparticles (SiNPs) (as described in Luo D and Saltzman W M. (2000). Nat Biotechnol 18:893-5).

HSC—Delivery to and Editing of Hematopoietic Stem Cells

In some embodiments, the engineered cells are engineered HSCs. The HSCs (e.g., one or more loci in the HSCs) may be engineered by a CRISPR-Cas system. Cas protein, advantageously codon-optimized for a eukaryotic cell and especially a mammalian cell, e.g., a human cell, for instance, HSC, and sgRNA targeting a locus or loci in HSC, e.g., the gene EMX1, may be prepared. These may be advantageously delivered via particles. The particles may be formed by the Cas protein and the sgRNA being admixed. The sgRNA and Cas protein mixture may be admixed with a mixture comprising or consisting essentially of or consisting of surfactant, phospholipid, biodegradable polymer, lipoprotein and alcohol, whereby particles containing the sgRNA and Cas protein were formed. The disclosure comprehends so making particles and particles from such a method as well as uses thereof.

More generally, particles may be formed using an efficient process. First, Cas protein and sgRNA targeting a gene may be mixed together at a suitable, e.g., 3:1 to 1:3 or 2:1 to 1:2 or 1:1 molar ratio, at a suitable temperature, e.g., 15-30° C., e.g., 20-25° C., e.g., room temperature, for a suitable time, e.g., 15-45 minutes, such as 30 minutes, advantageously in sterile, nuclease free buffer, e.g., 1×PBS. Separately, particle components such as or comprising a surfactant, e.g., cationic lipid, e.g., 1,2-dioleoyl-3-trimethylammonium-propane (DOTAP); phospholipid, e.g., dimyristoylphosphatidylcholine (DMPC); biodegradable polymer, such as an ethyleneglycol polymer or PEG, and a lipoprotein, such as a lowdensity lipoprotein, e.g., cholesterol may be dissolved in an alcohol, advantageously a C1-6 alkyl alcohol, such as methanol, ethanol, isopropanol, e.g., 100% ethanol. The two solutions may be mixed together to form particles containing the Cas-sgRNA complexes. In certain embodiments the particle may contain an HDR template. That may be a particle co-administered with sgRNA+Cas protein-containing particle, or e.g., in addition to contacting an HSC with an sgRNA+Cas protein-containing particle, the HSC may be contacted with a particle containing an HDR template, or the HSC may be contacted with a particle containing all of the sgRNA, Cas and the HDR template. The HDR template may be administered by a separate vector, whereby in a first instance the particle penetrates an HSC cell and the separate vector also penetrates the cell, wherein the HSC genome is modified by the sgRNA+Cas and the HDR template is also present, whereby a genomic locus is modified by the HDR. For instance, this may result in correcting a mutation.

After the particles are formed, HSCs in 96 well plates may be transfected with 15 ug Cas9 protein per well. Three days after transfection, HSCs were harvested, and the number of insertions and deletions (indels) at the locus may be quantified.

This demonstrates that HSCs can be modified using CRISPR-Cas targeting a genomic locus or loci of interest in the HSC. The HSCs that are to be modified can be in vivo, e.g., in an organism, for example a human or a non-human eukaryote, e.g., animal, such as fish, e.g., zebra fish, mammal, e.g., primate, e.g., ape, chimpanzee, macaque, rodent, e.g., mouse, rabbit, rat, canine or dog, livestock (cow/bovine, sheep/ovine, goat or pig), fowl or poultry, e.g., chicken. The HSCs that are to be modified can be in vitro, i.e., outside of such an organism. And, modified HSCs can be used ex vivo, i.e., one or more HSCs of such an organism can be obtained or isolated from the organism, optionally the HSC(s) can be expanded, the HSC(s) are modified by a composition comprising a CRISPR-Cas that targets a genetic locus or loci in the HSC, e.g., by contacting the HSC(s) with the composition, for instance, wherein the composition comprises a particle containing the CRISPR enzyme and one or more sgRNA that targets the genetic locus or loci in the HSC, such as a particle obtained or obtainable from admixing an sgRNA and Cas protein mixture with a mixture comprising or consisting essentially of or consisting of surfactant, phospholipid, biodegradable polymer, lipoprotein and alcohol (wherein one or more sgRNA targets the genetic locus or loci in the HSC), optionally expanding the resultant modified HSCs and administering to the organism the resultant modified HSCs. In some instances, the isolated or obtained HSCs may be from a first organism, such as an organism from a same species as a second organism, and the second organism can be the organism to which the resultant modified HSCs are administered, e.g., the first organism can be a donor (such as a relative, as in a parent or sibling) to the second organism. Modified HSCs may have genetic modifications to address or alleviate or reduce symptoms of a disease or condition state of an individual or subject or patient. Modified HSCs, e.g., in the instance of a first organism donor to a second organism, may have genetic modifications to have the HSCs have one or more proteins e.g. surface markers or proteins more like that of the second organism. Modified HSCs may have genetic modifications to simulate a disease or condition state of an individual or subject or patient and would be re-administered to a non-human organism so as to prepare an animal model. Expansion of HSCs is within the ambit of the skilled person from this disclosure and knowledge in the art, see e.g., Lee, "Improved ex vivo expansion of adult hematopoietic stem cells by overcoming CUL4-mediated degradation of HOXB4." Blood. 2013 May 16; 121 (20): 4082-9. doi: 10.1182/blood-2012-09-455204. Epub 2013 Mar. 21.

As indicated to improve activity, guide RNA (e.g., sgRNA) may be pre-complexed with the Cas protein, before formulating the entire complex in a particle. Formulations may be made with a different molar ratio of different components known to promote delivery of nucleic acids into cells (e.g. 1,2-dioleoyl-3-trimethylammonium-propane (DOTAP), 1,2-ditetradecanoyl-sn-glycero-3-phosphocholine (DMPC), polyethylene glycol (PEG), and cholesterol) For example DOTAP: DMPC: PEG: Cholesterol Molar Ratios may be DOTAP 100, DMPC 0, PEG 0, Cholesterol 0; or DOTAP 90, DMPC 0, PEG 10, Cholesterol 0; or DOTAP 90, DMPC 0, PEG 5, Cholesterol 5. DOTAP 100, DMPC 0, PEG 0, Cholesterol 0. The disclosure accordingly comprehends admixing sgRNA, Cas protein and components that form a particle, as well as particles from such admixing.

In an example embodiment, particles containing the Cas-sgRNA complexes may be formed by mixing Cas protein and one or more sgRNAs together, preferably at a 1:1 molar ratio, enzyme: guide RNA. Separately, the different components known to promote delivery of nucleic acids (e.g. DOTAP, DMPC, PEG, and cholesterol) are dissolved, preferably in ethanol. The two solutions are mixed together to form particles containing the Cas-sgRNA complexes. After the particles are formed, Cas-sgRNA complexes may be transfected into cells (e.g., HSCs). Bar coding may be applied. The particles, the Cas, and/or the sgRNA may be barcoded.

The disclosure also includes methods of preparing an sgRNA-and-Cas protein containing particle comprising admixing an sgRNA and Cas protein mixture with a mixture comprising or consisting essentially of or consisting of surfactant, phospholipid, biodegradable polymer, lipoprotein and alcohol. An embodiment comprehends an sgRNA-and-Cas protein containing particle from the method. An embodiment comprehends use of the particle in a method of modifying a genomic locus of interest, or an organism or a non-human organism by manipulation of a target sequence in a genomic locus of interest, comprising contacting a cell containing the genomic locus of interest with the particle wherein the sgRNA targets the genomic locus of interest; or a method of modifying a genomic locus of interest, or an organism or a non-human organism by manipulation of a target sequence in a genomic locus of interest, comprising contacting a cell containing the genomic locus of interest with the particle, wherein the sgRNA targets the genomic locus of interest. In these embodiments, the genomic locus of interest is advantageously a genomic locus in an HSC.

Methods of Using the Engineered Cells

The present disclosure further includes methods of using the engineered cells, e.g., for treating a disease in a subject. Such methods may include administering to the subject of the engineered cells disclosed herein.

Administration

In some embodiments, the methods include administering one or more engineered cells to a subject (e.g., a subject in need thereof).

In some cases, the engineered cells may be administered to the site of intended benefit is preferred. In some examples, the engineered cells may be administered intravascularly. Other routes of administration may include intratracheal delivery, intraventricular delivery, intrathecal delivery, intraosseous delivery, pulmonary delivery, buccal delivery, aerosol delivery, inhalational delivery, oral delivery, intraarterial delivery, intracerebral delivery, intraintestinal delivery, intracardiac delivery, subcutaneous delivery, intramuscular delivery, intraorbital delivery, intracapsular delivery, intraspinal delivery, intraperitoneal delivery, intrasternal delivery, intravesical delivery, intralymphatic delivery, intracavital delivery, vaginal delivery, rectal delivery, transurethral delivery, intradermal delivery, intraocular delivery, aural delivery, intramammary delivery, orthotopic delivery, intratracheal delivery, intralesional delivery, percutaneous delivery, endoscopical delivery, transmucosal delivery, sublingual delivery, and direct application on body surfaces (e.g., directly onto skin surface).

In some examples, the engineered cells are administered to the brain, e.g., intraventricularly. For example, the engineered cells may be administered to the cerebrospinal fluid (CSF) of a subject. In certain examples, the engineered cells may be administered to cerebral ventricle space. In some examples, the cells may be administered by lateral cerebro ventricular injection into the brain of a subject. The injection can be made, for example, through a burr hole made in the subject's skull. In certain examples, the cells and/or other pharmaceutical formulation may be administered through a surgically inserted shunt into the cerebral ventricle of a subject. For example, the injection may be made into the lateral ventricles, which are larger, even though injection into the third and fourth smaller ventricles can also be made.

In some examples, the engineered cells are administered intrathecally, e.g., to the spinal canal, the subarachnoid space, the lumbar area, and/or the cisterna magna. Intrathecal administration may include delivering the cells directly into the cerebrospinal fluid of a subject, by techniques including lateral cerebroventricular injection through a burrhole or cisternal or lumbar puncture or the like. The term "lumbar region" is intended to include the area between the third and fourth lumbar (lower back) vertebrae and, more inclusively, the L2-S1 region of the spine. The term "cisterna magna" is intended to include access to the space around and below the cerebellum via the opening between the skull and the top of the spine. The term "cerebral ventricle" is intended to include the cavities in the brain that are continuous with the central canal of the spinal cord.

In some embodiments, the cells may be placed in a delivery device which facilitates introduction by injection or implantation into the subjects. Examples of such delivery devices include tubes, e.g., catheters, endoscopic delivery devices, infusion pumps, or reservoir and catheters for intraventricular injection. The tubes may additionally have a needle.

The cells may be prepared for delivery in a variety of different forms. For example, the cells may be suspended in a solution or gel or embedded in a support matrix when contained in such a delivery device. The cells may be mixed with a pharmaceutically acceptable carrier or diluent in which the cells of the disclosure remain viable. Pharmaceutically acceptable carriers and diluents include saline, aqueous buffer solutions, solvents and/or dispersion media. The solution may be sterile and fluid. The solution may be stable under the conditions of manufacture and storage and preserved against the contaminating action of microorganisms such as bacteria and fungi through the use of, for example, parabens, chlorobutanol, phenol, ascorbic acid, thimerosal, and the like. Solutions may be prepared by incorporating cells as described herein in a pharmaceutically acceptable carrier or diluent and, as required, other ingredients, followed by filtered sterilization.

In some embodiments, the cells are introduced into the subject as part of a cell aggregate (e.g., a pancreatic islet), tissue, or organ, e.g., as part of an organ transplant method.

Dosage

The cells may be introduced to the subject at a suitable dose. In some cases, from $4\times10^5$ to $9\times10^6$ cells per kilogram body weight of the subject. For example, from $4\times10^5$ to $2\times10^6$, from $1\times10^6$ to $3\times10^6$, from $2\times10^6$ to $4\times10^6$, from $3\times10^6$ to $5\times10^6$, from $4\times10^6$ to $6\times10^6$, from $5\times10^6$ to $7\times10^6$, from $6\times10^6$ to $8\times10^6$, or from $7\times10^6$ to $9\times10^6$ cells per kilogram body weight of the subject.

Diseases and Conditions

The method may be used for treating, preventing, or ameliorating one or more diseases or conditions. In some cases, the diseases or conditions include nervous system-related diseases.

In some embodiments, the diseases or conditions include Rett syndrome. For example, by editing HSC cells from patients with Rett syndrome, related genetic variants (e.g., MeCP2 mutation) may be corrected. The corrected HSCs may be transplanted back into the patient (e.g., by intraventricular or intravascular delivery) to engraft healthy microglia in the brain to correct the condition (see e.g., Derecki et al., Nature. 2012 Mar. 18; 484 (7392): 105-9).

In some embodiments, the diseases or conditions include Schizophrenia. For example, by editing HSC cells from Schizophrenia patients to correct genetic difference that cause elevated expression of one or more related genes (e.g., complement protein C4), the edited HSCs may be transplanted back into the patient to treat Schizophrenia.

In some embodiments, the diseases or conditions include Hurler's syndrome. For example, by editing HSC cells from patients with Hurler's syndrome, related genetic variants (e.g., IDUA gene) may be corrected. The corrected HSCs may be transplanted back into the patient to engraft healthy microglia in the brain to correct the condition.

In some embodiments, the diseases or conditions include lysosomal storage diseases. Examples of such diseases include Hurler's syndrome, aspartylglucosaminuria, cholesterol ester storage disease, Wolman disease, cystinosis, Danon disease, Fabry disease, Farber lipogranulomatosis, Farber disease, fucosidosis, galactosialidosis types I/II, Gaucher disease types I/II/III, globoid cell leukodystrophy, Krabbe disease, glycogen storage disease II, Pompe disease, GM1-gangliosidosis types I/II/III, GM2-gangliosidosis type I, Tay Sachs disease, GM2-gangliosidosis type II, Sandhoff disease, GM2-gangliosidosis, .alpha.-mannosidosis types I/II, .beta.-mannosidosis, metachromatic leukodystrophy, mucolipidosis type I, sialidosis types I/II, mucolipidosis types II/III, I-cell disease, mucolipidosis type IIIC pseudo-Hurler polydystrophy, mucopolysaccharidosis type I, mucopolysaccharidosis type II, Hunter syndrome, mucopolysaccharidosis type IIIA, Sanfilippo syndrome, mucopolysaccharidosis type IIIB, mucopolysaccharidosis type IIIC, mucopolysaccharidosis type IIID, mucopolysaccharidosis type IVA, Morquio syndrome, mucopolysaccharidosis type IVB, mucopolysaccharidosis type VI, mucopolysaccharidosis type VII, Sly syndrome, mucopolysaccharidosis type IX, multiple sulfatase deficiency, neuronal ceroid lipofuscinosis, CLN1 Batten disease, CLN2 Batten disease, Niemann-Pick disease types A/B, Niemann-Pick disease type C1, Niemann-Pick disease type C2, pycnodysostosis, Schindler disease types I/II, and sialic acid storage disease. In some examples, the lysosomal storage disease is Hurler's syndrome.

In some embodiments, the diseases or conditions include Schizophrenia. Examples of Schizophrenia include paranoid type, disorganized type, catatonic type, undifferentiated type, residual type, post-schizophrenic depression, simple schizophrenia, and cenesthopathic schizophrenia and schizophreniform disorder NOS.

In some embodiments, the diseases or conditions include autism spectrum disorders. Examples of autism spectrum disorders include high-functioning autism, autistic disorder, Asperger's syndrome, pervasive developmental disorder, and Rett syndrome. In certain examples, the diseases or conditions include Rett syndrome.

The compositions and methods may be used for treating any diseases or conditions associated microglial cells. Examples of such diseases or conditions include Alzheimer's disease, Parkinson's disease, Multiple sclerosis, as well as cardiac diseases, glaucoma, and viral and bacterial infections, neuropathic pain, neuroinflammation, viral encephalitis, acquired immune deficiency syndrome (AIDS), and Multiple Sclerosis (MS). Such diseases and conditions also include autoimmune brain diseases, e.g., disease where a patient's immune system attacks the brain, for example, Autoimmune encephalitis, Autoimmune-related epilepsy, Central nervous system (CNS) vasculitis, Hashimoto's encephalopathy (steroid-responsive encephalopathy), Neuromyelitis optica, Optic neuritis, Neurosarcoidosis, Neuro-Behcet's disease, and Cerebral lupus.

Enzyme Replacement Therapy

In some embodiments, the methods may include administering enzyme replacement therapy by administering the engineered cells to a subject (a subject in need thereof). Enzyme replacement therapy (ERT) includes any therapeutic strategy that corrects an enzyme deficiency by providing the missing enzyme. In some embodiments, the engineered cells or progeny cells thereof may produce a protein suitable for the enzyme replacement therapy.

The present application also provides aspects and embodiments as set forth in the following numbered Statements:

Statement 1. A composition comprising an engineered cell designed to infiltrate or engraft in the central nervous system (CNS) of a subject and differentiate into a microglial cell that treats and/or ameliorates a disease or disorder of the CNS in the subject.

Statement 2. The composition of statement 1, wherein the engineered cell comprises a hematopoietic stem cell (HSC).

Statement 3. The composition of statement 1 or 2, wherein the engineered cell is capable of engrafting in the brain or spinal cord.

Statement 4. The composition of any one of the proceeding statements, wherein the engineered cell is designed to treat or ameliorate a lysosomal storage disease.

Statement 5. The composition of any one of the proceeding statements, wherein the engineered cell is engineered to produce a protein suitable for enzyme replacement therapy.

Statement 6. The composition of statement 4, wherein the lysosomal storage disease is Hurler's syndrome.

Statement 7. The composition of any one of the proceeding statements, wherein the engineered cell is designed to treat or ameliorate schizophrenia.

Statement 8. The composition of any one of the proceeding statements, wherein the engineered cell is designed to treat or ameliorate an autism spectrum disorder.

Statement 9. The composition of statement 8, wherein the autism spectrum disorder is Rett Syndrome.

Statement 10. The composition of any one of the proceeding statements, wherein the engineered cell is designed to treat Alzheimer's disease.

Statement 11. The composition of any one of the proceeding statements, wherein the engineered cell is from or derived from the subject.

Statement 12. The composition of any one of the proceeding statements, wherein the engineered cell is from or derived from a donor subject of the same species as the subject.

Statement 13. The composition of any one of the proceeding statements, wherein the engineered cell is from or derived from a donor subject of a different species as the subject.

Statement 14. The composition of any one of the proceeding statements, wherein one or more immunogenic genes in the engineered cell is deleted.

Statement 15. The composition of statement 14, wherein one or more of immunogenic genes comprises Ox40, GITR, 4-1BB, CD2, CD28, ICOS, CD27, HVEM, SLAM, CD226, PD1, CTLA4, LAG3, TIM3, B7-H1, PD-L1, TLT-2, CD30, CD160, BTLA, LAIR1, 2B4, CD244, TCR, PD-1, CTLA4, LAG-3, CCR5, PCSK9, APOC3, TRAC, TRBC, or any combination thereof.

Statement 16. The composition of any one of the proceeding statements, wherein the engineered cell comprises one or more tolerogenic factors.

Statement 17. The composition of claim 16, wherein the one or more tolerogenic factors comprises HLA-C, HLA-E, HLA-F, HLA-G, PD-L1, CTLA-4-Ig, CD47, CI-inhibitor, and IL-35, HLA-A, HLA-B, HLA-C, or any combination thereof.

Statement 18. A method of making an engineered cell according to any one of the proceeding statements, wherein the method comprises delivering to a hematopoietic stem cell (HSC) a gene editing system modifying one or more genes in the HSC.

Statement 19. The method of statement 18, wherein the gene editing system is a CRISPR-Cas system.

Statement 20. The method of statement 19, wherein the CRISPR-Cas system comprises: a CRISPR system guide or a polynucleotide encoding the guide, a CRISPR protein or a polynucleotide encoding the CRISPR protein, and optionally a template or a polynucleotide encoding the template; wherein the guide directs sequence specific binding of a CRISPR complex to a target sequence in a genomic locus of the HSC; wherein the template comprises a nucleic acid sequence capable of modifying the target sequence; and whereby the target sequence of the HSC is modified.

Statement 21. The method of statement 18, wherein the target sequence comprises a protein encoding sequence of the HSC.

Statement 22. The method of statement 20 or 21, wherein the target sequence comprises a regulatory sequence of the HSC.

Statement 23. A method of treating a disease or disorder of the CNS in a subject, which comprises administering to the subject the composition of any one of statements 1-17.

Statement 24. The method of statement 23, wherein the composition is delivered intravascularly or intrathecally.

Statement 25. The method of statement 23 or 24, wherein the composition is delivered to the cerebrospinal fluid (CSF) of the subject.

Statement 26. The method of any one of statements 23-25, wherein the composition comprises an syngeneic cell.

Statement 27. The method of any one of statements 23-26, wherein the composition comprises an allogeneic cell.

Statement 28. Use of the composition of any one of statements 1-17 for the preparation of a medicament for the treatment of a disease or disorder of the CNS in a subject.

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A composition for treating or ameliorating a disease or disorder of a subject's central nervous system (CNS), comprising:
   a cell population comprising stem cell-derived microglial cells genetically engineered to enhance CNS engraftment efficiency,
   wherein the stem cell-derived microglial cells are genetically engineered:
   to abrogate expression of CD26 and/or stromal cell-derived factor-1 genes, and one or more immunogenic genes chosen from OX40, GITR, 4-1BB, CD2, CD28, ICOS, CD27, HVEM, SLAM, CD226, PD1, CTLA4, LAG3, TIM3, B7-H1, PD-L1, TLT-2, CD30, CD160, BTLA, LAIR1, 2B4, CD244, TCR, PD-1, CTLA4, LAG-3, CCR5, PCSK9, APOC3, TRAC, TRBC, or any combination thereof, or
   to abrogate expression of CD26 and/or stromal cell-derived factor-1 genes and induce the expression of one or more tolerogenic factors chosen from HLA-C, HLA-E, HLA-F, HLA-G, PD-L1, CTLA-4-Ig, CD47, CI-inhibitor, IL-35, HLA-A, HLA-B, or any combination thereof.

2. The composition of claim 1, wherein the cell population comprising the genetically engineered stem cell-derived microglial cells is generated by ex vivo differentiation of genetically engineered a hematopoietic stem cell (HSC).

3. The composition of claim 2, wherein the hematopoietic stem cells (HSCs) are obtained from the subject, from a donor of the same species as the subject, or from a donor of a different species than the subject.

4. The composition of claim 1, wherein the cell population comprising stem cell-derived microglial cells is genetically engineered to express a therapeutic protein for enzyme replacement therapy.

5. A method for generating a cell population comprising stem cell-derived microglial cells genetically engineered to enhance CNS engraftment efficiency, comprising
   delivering a gene editing system to a hematopoietic stem cell (HSC) population,
   wherein the gene editing system modifies target nucleotide sequences
   to abrogate microglial cell expression of CD26 and/or stromal cell-derived factor-1 gene and one or more immunogenic genes chosen from OX40, GITR, 4-1BB, CD2, CD28, ICOS, CD27, HVEM, SLAM, CD226, PD1, CTLA4, LAG3, TIM3, B7-H1, PD-L1, TLT-2, CD30, CD160, BTLA, LAIR1, 2B4, CD244, TCR, PD-1, CTLA4, LAG-3, CCR5, PCSK9, APOC3, TRAC, TRBC, or any combination thereof, or to abrogate microglial cell expression of CD26 and/or stromal cell-derived factor-1 gene and induce microglial cell expression of one or more tolerogenic factors chosen from HLA-C, HLA-E, HLA-F, HLA-G, PD-L1, CTLA-4-Ig, CD47, CI-inhibitor, IL-35, HLA-A, HLA-B, or any combination thereof, and differentiating the modified HSC population ex vivo to produce the cell population of genetically engineered stem cell-derived microglial cells.

6. The method of claim 5, wherein the gene editing system is a CRISPR-Cas system.

7. The method of claim 6, wherein the CRISPR-Cas system comprises:
   a CRISPR system guide or a polynucleotide encoding the guide;
   a CRISPR protein or a polynucleotide encoding the CRISPR protein; and
   optionally a template or a polynucleotide encoding the template,
   wherein the guide directs sequence-specific binding of a CRISPR complex to a target sequence in a genomic locus of the HSC,
   wherein the template comprises a nucleic acid sequence capable of modifying the target sequence, and
   wherein the target sequence of the HSC is modified.

8. The method of claim 5, wherein the target sequence comprises a protein-encoding sequence or a regulatory sequence of the CD26 and/or stromal cell-derived factor-1 gene, and one or more immunogenic genes chosen from OX40, GITR, 4-1BB, CD2, CD28, ICOS, CD27, HVEM, SLAM, CD226, PD1, CTLA4, LAG3, TIM3, B7-H1, PD-L1, TLT-2, CD30, CD160, BTLA, LAIR1, 2B4, CD244, TCR, PD-1, CTLA4, LAG-3, CCR5, PCSK9, APOC3, TRAC, TRBC, or one or more tolerogenic factors chosen from HLA-C, HLA-E, HLA-F, HLA-G, PD-L1, CTLA-4-Ig, CD47, CI-inhibitor, IL-35, HLA-A, HLA-B.

9. A method of treating a disease or disorder of the central nervous system (CNS) in a subject, comprising administering a cell population comprising stem cell-derived microglial cells genetically engineered to enhance CNS engraftment efficiency to the subject in need thereof,
   wherein the stem cell-derived microglial cells are genetically engineered:
   to abrogate expression of CD26 and/or stromal cell-derived factor-1 genes, and one or more immunogenic genes chosen from OX40, GITR, 4-1BB, CD2, CD28, ICOS, CD27, HVEM, SLAM, CD226, PD1, CTLA4, LAG3, TIM3, B7-H1, PD-L1, TLT-2, CD30, CD160, BTLA, LAIR1, 2B4, CD244, TCR, PD-1, CTLA4, LAG-3, CCR5, PCSK9, APOC3, TRAC, TRBC, or any combination thereof, or to abrogate expression of CD26 and/or stromal cell-derived factor-1 genes and induce the expression of one or more tolerogenic factors chosen from HLA-C, HLA-E, HLA-F, HLA-G, PD-L1, CTLA-4-Ig, CD47, CI-inhibitor, IL-35, HLA-A, HLA-B, or any combination thereof.

10. The method of claim 9, wherein the composition of genetically engineered stem cell-derived microglial cells is administered intravascularly or intrathecally.

11. The method of claim 9, wherein the composition of genetically engineered stem cell-derived microglial cells is delivered to the subject's cerebrospinal fluid (CSF).

12. The method of claim 9, wherein the composition of genetically engineered stem cell-derived microglial cells comprises syngeneic cells or allogeneic cells.

13. The method of claim 9, wherein the cell population comprising the genetically engineered stem cell-derived microglial cells is generated by ex vivo differentiation of genetically engineered a hematopoietic stem cell (HSC).

14. The method of claim 9, wherein the hematopoietic stem cells (HSCs) are obtained from the subject, from a donor of the same species as the subject, or from a donor of a different species than the subject.

15. The method of claim 9, wherein the cell population comprising stem cell-derived microglial cells is genetically engineered to express a therapeutic protein for enzyme replacement therapy.

16. The method of claim 9, wherein the composition of genetically engineered stem cell-derived microglial cells is capable of brain or spinal cord engraftment.

17. The method of claim 9, wherein the composition of genetically engineered stem cell-derived microglial cells is engineered to treat or ameliorate a lysosomal storage disease, schizophrenia, or an autism spectrum disorder.

18. The method of claim 17, wherein the lysosomal storage disease is Hurler's syndrome.

19. The method of claim 17, wherein the autism spectrum disorder is Rett Syndrome.

20. The method of claim 9, wherein the composition of genetically engineered stem cell-derived microglial cells is engineered to treat Alzheimer's disease.

* * * * *